(12) United States Patent
Yamanashi et al.

(10) Patent No.: US 10,736,499 B2
(45) Date of Patent: *Aug. 11, 2020

(54) IMAGE ANALYSIS APPARATUS, IMAGE ANALYSIS SYSTEM, AND METHOD FOR OPERATING IMAGE ANALYSIS APPARATUS

(71) Applicant: OLYMPUS CORPORATION, Tokyo (JP)

(72) Inventors: Momoko Yamanashi, Tachikawa (JP); Tetsuhiro Yamada, Hino (JP); Toshio Nakamura, Hachioji (JP); Ryuichi Toyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 174 days.

This patent is subject to a terminal disclaimer.

(21) Appl. No.: 16/034,831

(22) Filed: Jul. 13, 2018

(65) Prior Publication Data
US 2018/0333045 A1 Nov. 22, 2018

Related U.S. Application Data
(63) Continuation of application No. PCT/JP2016/084940, filed on Nov. 25, 2016.

(30) Foreign Application Priority Data
Jan. 15, 2016 (JP) ................................ 2016-006197

(51) Int. Cl.
*G06T 1/00* (2006.01)
*A61B 1/04* (2006.01)
(Continued)

(52) U.S. Cl.
CPC ............ *A61B 1/04* (2013.01); *A61B 1/00009* (2013.01); *A61B 1/0638* (2013.01);
(Continued)

(58) Field of Classification Search
None
See application file for complete search history.

(56) References Cited

U.S. PATENT DOCUMENTS

2004/0019253 A1* 1/2004 Tsujita ..................... A61B 1/04
600/118
2009/0074269 A1 3/2009 Nishimura et al.
(Continued)

FOREIGN PATENT DOCUMENTS

EP 1994878 A1 11/2008
EP 2138977 A2 12/2009
(Continued)

OTHER PUBLICATIONS

International Search Report dated Feb. 21, 2017 issued in PCT/JP2016/084940.

*Primary Examiner* — Delomia L Gilliard
(74) *Attorney, Agent, or Firm* — Scully, Scott, Murphy & Presser, P.C.

(57) ABSTRACT

A video processor receives first and second images respectively acquired by an endoscope at first and second timings before and after a predetermined function is applied to a subject, generates first and second correction images respectively using first and second images, generates first and second post-correction images respectively obtained by causing the first and second correction images to act on the first and second images, extracts color components in the second post-correction image to find first and second distribution characteristic values, and calculates a degree of change of the second distribution characteristic value from the first distribution characteristic value.

16 Claims, 18 Drawing Sheets

(51) Int. Cl.
*G02B 23/24* (2006.01)
*A61B 1/06* (2006.01)
*A61B 1/00* (2006.01)
*G06T 1/20* (2006.01)
*G06T 1/60* (2006.01)

(52) U.S. Cl.
CPC ............ *A61B 1/0646* (2013.01); *G02B 23/24* (2013.01); *G06T 1/20* (2013.01); *G06T 1/60* (2013.01); *A61B 1/00002* (2013.01)

(56) References Cited

U.S. PATENT DOCUMENTS

| | | | |
|---|---|---|---|
| 2009/0079876 A1* | 3/2009 | Takeshima | G06T 3/4069 348/699 |
| 2009/0322907 A1* | 12/2009 | Takahashi | A61B 1/00004 348/234 |
| 2012/0114203 A1 | 5/2012 | Hirota | |
| 2013/0012794 A1* | 1/2013 | Zeng | A61B 1/00186 600/328 |
| 2014/0334698 A1* | 11/2014 | Tanaka | A61B 1/00009 382/128 |
| 2018/0218233 A1* | 8/2018 | Yamanashi | G02B 23/24 |

FOREIGN PATENT DOCUMENTS

| | | |
|---|---|---|
| EP | 2457494 A1 | 5/2012 |
| EP | 2815692 A1 | 12/2014 |
| JP | 2004-000505 A | 1/2004 |
| JP | 2007-502185 A | 2/2007 |
| JP | 2010-005056 A | 1/2010 |
| JP | 2011-024727 A | 2/2011 |
| JP | 2013-521900 A | 6/2013 |
| JP | 5242381 B2 | 7/2013 |
| JP | 2014-171535 A | 9/2014 |
| WO | WO 2007/119297 A1 | 10/2007 |
| WO | WO 2011/010598 A1 | 1/2011 |
| WO | WO 2011/113162 A1 | 9/2011 |
| WO | WO 2014/073527 A1 | 5/2014 |

\* cited by examiner

IMAGE ANALYSIS APPARATUS, IMAGE ANALYSIS SYSTEM, AND METHOD FOR OPERATING IMAGE ANALYSIS APPARATUS

CROSS REFERENCE TO RELATED APPLICATION

This application is a continuation application of PCT/JP2016/084940 filed on Nov. 25, 2016 and claims benefit of Japanese Application No. 2016-6197 filed in Japan on Jan. 15, 2016, the entire contents of which are incorporated herein by this reference.

BACKGROUND OF THE INVENTION

1. Field of the Invention

The present invention relates to an image analysis apparatus that analyzes a change of a subject from time-sequentially acquired images of the subject, an image analysis system, and a method for operating the image analysis apparatus.

2. Description of Related Art

Various techniques for analyzing a change of a subject from time-sequentially acquired images of the subject have been conventionally proposed.

For example, Japanese Patent Application Laid-Open Publication No. 2010-5056 discloses an image acquisition apparatus that picks up a normal image of an object to be observed by an image pickup device, and subjects an image signal outputted from the image pickup device to spectral image processing, to generate a spectral estimation image signal having a predetermined wavelength.

In the image acquisition apparatus, a spectral estimation image signal having a specific wavelength relating to a medicinal solution to be administered to the object to be observed is generated as a spectral estimation image signal for acquiring luminance information in a spectral image generation unit based on the image signal outputted from the image pickup device.

Furthermore, in the image acquisition apparatus, each piece of luminance information about spectral estimation image signals for acquiring luminance information, which have been generated at predetermined time intervals, is acquired by a luminance information acquisition unit. In a display apparatus, an image is displayed based on a rate of change in the luminance information.

Japanese Patent Application Laid-Open Publication No. 2007-502185 describes an image analysis method for picking up a digital image of a dental tissue, determining for each of a plurality of pixels within the digital image a first component value of a color of the pixel and a second component value of the color of the pixel, and calculating a first function value (e.g., R/G) of the pixel based on the first component value and the second component value.

SUMMARY OF THE INVENTION

An image processing apparatus according to an aspect of the present invention includes a processor including hardware, in which the processor receives a first image of a subject acquired by an endoscope at a first timing and a second image of the subject acquired by the endoscope at a second timing later than the first timing, generates first brightness distribution correction data for correcting a slope of a brightness distribution of the received first image using the first image and generates second brightness distribution correction data for correcting a slope of a brightness distribution of the second image using the second image, generates a first processed image acquired by causing the first brightness distribution correction data to act on the first image and a second processed image acquired by causing the second brightness distribution correction data to act on the second image, analyzes a degree of change between the first processed image and the second processed image, and extracts areas respectively surrounded by closed curves extracted from the first and second images to generates the first and second brightness distribution correction data based on a size of each of the extracted areas.

An image processing system according to another aspect of the present invention includes the above-described endoscope which is inserted into a subject to pick up and acquire an image within the subject, and the image analysis apparatus according to the one aspect.

An image processing method according to still another aspect of the present invention includes the steps of receiving a first image of a subject acquired by an endoscope at a first timing and a second image of the subject acquired by the endoscope at a second timing later than the first timing, generating first brightness distribution correction data for correcting a slope of a brightness distribution of the received first image using the first image and generating second brightness distribution correction data for correcting a slope of a brightness distribution of the second image using the second image, generating a first processed image obtained by causing the first brightness distribution correction data to act on the first image and a second processed image obtained by causing the second brightness distribution correction data to act on the second image, and analyzing a degree of change between the first processed image and the second processed image, in which in the step of generating the first and second brightness distribution correction data, areas respectively surrounded by closed curves extracted from the first and second images are extracted, and the first and second brightness distribution correction data are generated based on a size of each of the extracted areas.

DETAILED DESCRIPTION OF PREFERRED EMBODIMENTS

Figure 1:
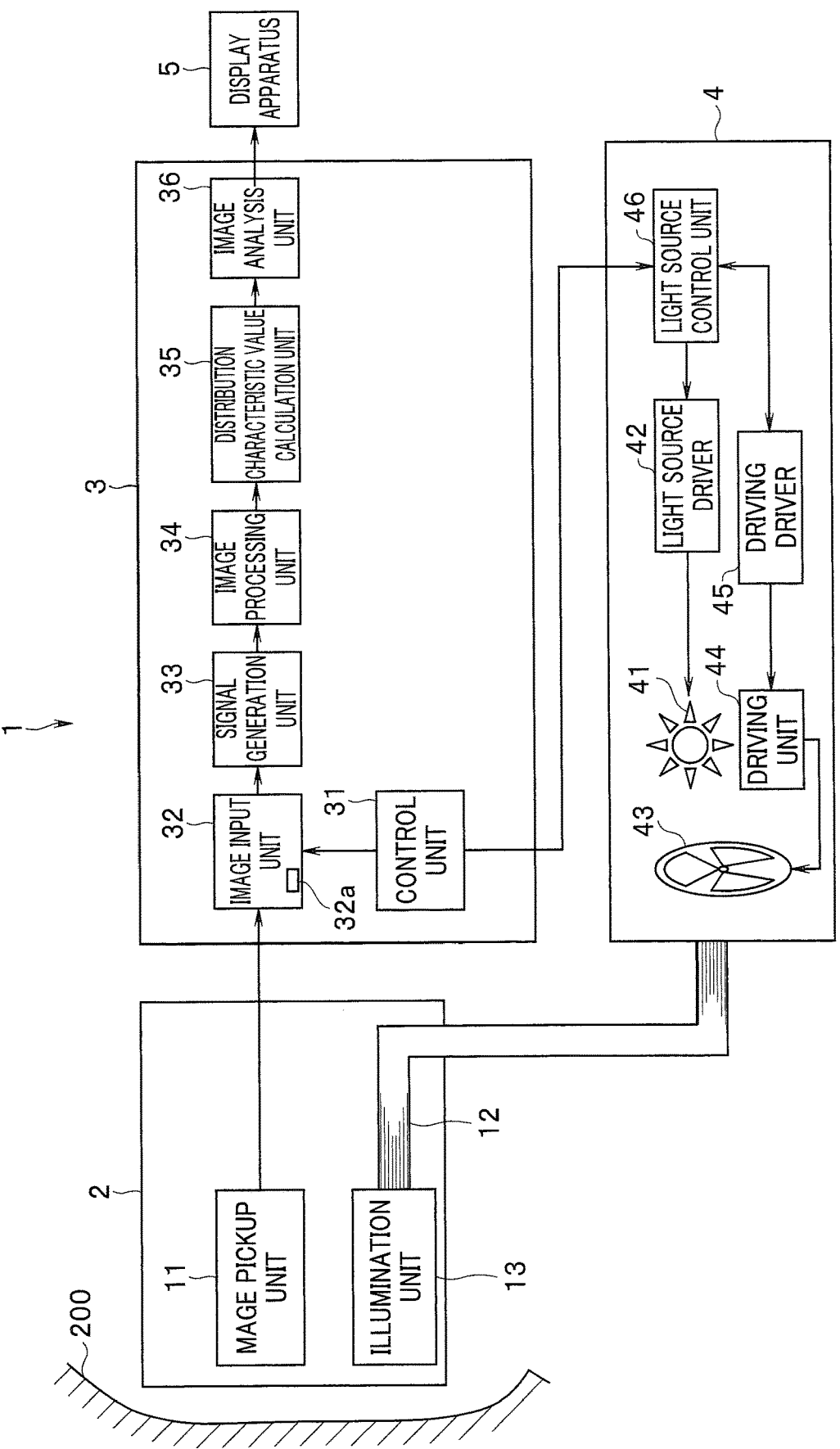
FIG. 1 is a block diagram illustrating a schematic configuration of an image analysis system according to a first embodiment of the present invention.

Embodiments of the present invention will be described below with reference to the drawings.

Note that in the following description, the same elements are assigned an identical reference numeral. Further, it should be noted that the drawings are schematic, and a relationship between a thickness and a width of each of units, a proportion of each of the units, and the like respectively differ from actual ones. Also, among the drawings, portions, which differ in size and proportion, are respectively included.

First Embodiment (System Configuration)

FIG. 1 is a block diagram illustrating a schematic configuration of an image analysis system according to a first embodiment of the present invention.

Note that in an embodiment illustrated below, an endoscope system and a video processor will be respectively described as examples of an "image analysis system" and an "image analysis apparatus".

As illustrated in FIG. 1, an endoscope system 1 as an image analysis system mainly includes an endoscope 2, a video processor 3 as an image analysis apparatus, a light source apparatus 4, and a display apparatus 5.

The endoscope system 1 can not only perform normal light observation with white light but also can cope with narrow band imaging (hereinafter referred to as NBI) as the entire system in the present embodiment.

The endoscope 2 includes an elongated insertion section (not illustrated) to be inserted into a subject 200, and further includes an image pickup unit 11 disposed in a distal end portion of the insertion section and configured to pick up an image of the subject 200 to acquire an image signal, a light guide 12 configured to transmit illumination light from the light source apparatus 4, and an illumination unit 13 configured to irradiate the subject 200 with the illumination light. A subject image acquisition section configured to acquire an image of the subject and an illumination window configured to illuminate the subject are arranged on the same surface at a distal end of the distal end portion of the insertion section in the endoscope 2.

Note that although the illumination is performed using the light guide here, a plurality of light emitting elements such as light emitting diodes (hereinafter referred to as LEDs) may be provided in the distal end portion of the insertion section to irradiate illumination light of each of the plurality of LEDs.

A distal end hood or a distal end attachment, for example, is mountable on the distal end of the endoscope 2 to reduce the number of noise components to perform enlarged observation by NBI.

Furthermore, in the present embodiment, the image of the subject is time-sequentially acquired in the endoscope 2 to apply a predetermined load (predetermined function) to the subject and time-sequentially observe a change of the subject throughout before and after the load (function) is applied.

Here, the above-described "predetermined function" applied to the subject is, for example, administration of a medicinal solution to the subject. Note that in the present embodiment, the above-described "medicinal solution" means, for example, normal saline, glucose, or liquid fat (fat emulsion, etc.). Spraying of glucose will be described as a specific example of the load (function), described below.

The above-described "predetermined function" is not limited to the above-described administration of the medicinal solution but may be a function such as intravenous injection, air feeding into a body cavity, or physical contact of a treatment instrument or an endoscope itself with a body.

Note that setting of brightness of the endoscope 2 desirably remains the same to more accurately capture the change of the subject before and after the predetermined function is applied to the subject. Therefore, an image of the subject is preferably acquired without dimming a light source before and after the predetermined function is applied to the subject but by making an amount of emitted light from the light source constant.

The endoscope 2 is provided with an operation section (not illustrated). A user of the endoscope system 1 as an inspector can perform acquisition of an image of the subject 200 and a bending operation of a bending portion provided in the distal end portion of the insertion section, for example, by operating operation members such as a freeze button, a release button, and a bending operation knob provided in the operation section.

The light source apparatus 4 is connected to the endoscope 2 and the video processor 3. The light source apparatus 4 includes a light source 41, a light source driver 42, a rotating filter 43, a driving unit 44, a driving driver 45, and a light source control unit 46.

The light source 41 is configured using a white LED, a xenon lamp, or the like, and produces white light under control of the light source control unit 46. The light source driver 42 causes the light source 41 to produce white light under control of the light source control unit 46. The light produced by the light source 41 is radiated from the illumination unit 13 in the endoscope 2 via the rotating filter 43, a collecting lens (not illustrated), and the light guide 12.

The rotating filter 43 is arranged on an optical path of the white light emitted by the light source 41, and rotates, to transmit light corresponding to narrow band imaging (NBI) upon receipt of the white light emitted by the light source 41, i.e., narrow-banded light including respective wavelength ranges of blue light having a wavelength in the vicinity of 415 nm (e.g., approximately 400 nm to 440 nm) and green light having a wavelength in the vicinity of 540 nm (e.g., approximately 525 nm to 555 nm). Note that a filter for normal light observation is omitted in FIG. 1.

Accordingly, an image obtained in the endoscope 2 is an image of reflected light when the subject is illuminated with illumination light in a narrower predetermined wavelength band than the white light.

Here, generally in observation by NBI adopted in the present embodiment, blue and green narrow band lights are radiated onto a surface of intestinal mucosa, to display an endoscope image obtained by converting blue reflected light into blue and green reflected lights and converting green reflected light into red reflected light on the display apparatus 5.

Note that although two narrow band lights, i.e., blue light having a wavelength in the vicinity of 415 nm and green light having a wavelength in the vicinity of 540 nm are used for NBI in the present embodiment, only either one of the two narrow band lights, i.e., blue light having a wavelength in the vicinity of 415 nm and green light having a wavelength in the vicinity of 540 nm may be used, and one or two or more narrow band lights in other wavelength bands may be further used.

The light source apparatus 4 emits white light as illumination light when the endoscope system 1 is set to a normal light observation mode, and emits narrow-banded light as illumination light when the endoscope system 1 is set to a narrow band light observation mode.

The driving driver 45 supplies a predetermined current to the driving unit 44 under control of the light source control unit 46, and the driving unit 44 operates the rotating filter 43 to rotate using a synchronization signal transmitted from the video processor 3 as a reference under control of the light source control unit 46.

The display apparatus 5 is connected to the video processor 3, and has a function of receiving a subject image generated by the video processor 3, for example, from the video processor 3 via a predetermined video cable.

(Configuration of Video Processor)

The video processor 3 to which the endoscope 2 and the light source apparatus 4 are connected includes a control unit 31 configured to integrally control the entire endoscope system 1 and an image input unit 32, a signal generation unit 33, an image processing unit 34, a distribution characteristic value calculation unit 35, and an image analysis unit 36 which are controlled by the control unit 31.

Note that the video processor 3 functions as a signal processing apparatus of an image pickup signal from the image pickup unit 11 in the endoscope 2 while functioning as an "image analysis apparatus".

The video processor 3 is configured by including a central processing unit (hereinafter referred to as a CPU), a ROM, a RAM, a hard disk device, and the like. The control unit 31 implements operation control of the entire endoscope system 1 and each of the functions when the CPU reads out and executes various types of programs stored in the ROM or the like.

Operation control of the image input unit 32, the signal generation unit 33, the image processing unit 34, the distribution characteristic value calculation unit 35, and the image analysis unit 36 is also performed by the CPU reading out and executing the various types of programs stored in the ROM or the like.

The image input unit 32 receives the image pickup signal from the image pickup unit 11 in the endoscope 2 and generates image data for each frame from the image pickup signal. That is, an image of the subject time-sequentially acquired by the image pickup unit 11 is inputted to the image input unit 32, and the image input unit 32 generates image data for each frame. The image input unit 32 also has a function of sorting inputted image data in chronological order, as described below.

The image input unit 32 includes a memory 32a such as a RAM configured to generate and store image data corresponding to a plurality of frames by an amount corresponding to a predetermined time period or corresponding to a predetermined number of frames based on the image pickup signal from the endoscope 2 continuously inserted into the subject, and outputs the image data corresponding to the frame designated by a control signal from the control unit 31.

The image input unit 32 receives as input a first image IMG1 acquired at a first timing designated by the control signal from the control unit 31 and a second image IMG2 acquired at a second timing later than the first timing among the generated image data corresponding to the plurality of frames, and outputs the images to the signal generation unit 33.

The signal generation unit 33 generates, from respective image data of the first image IMG1 and the second image IMG2 from the image input unit 32, respective image data of correction images CP for the images.

Figure 2:
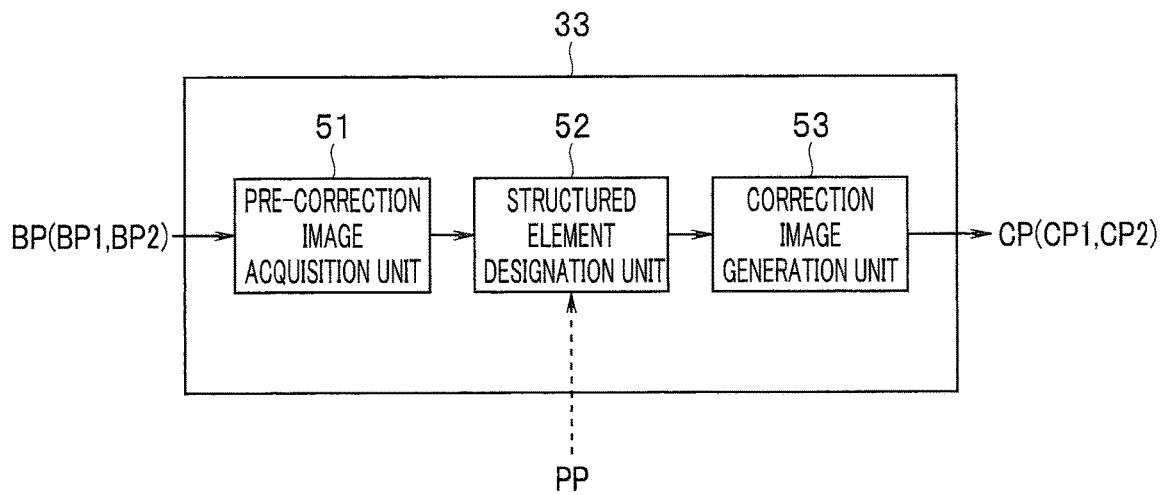
FIG. 2 is a block diagram illustrating a configuration of a signal generation unit 33 according to the first embodiment of the present invention.

FIG. 2 is a block diagram illustrating a configuration of the signal generation unit 33. The signal generation unit 33 includes a pre-correction image acquisition unit 51, a structured element designation unit 52, and a correction image generation unit 53.

The pre-correction image acquisition unit 51 is a processing unit configured to acquire respective image data in analysis target areas AA of the first image IMG1 and the second image IMG2 from the image input unit 32. That is, a pre-correction image BP as an image before a brightness distribution due to a light distribution characteristic of illumination light, for example, is corrected for each of the first image IMG1 and the second image IMG2 is inputted to the pre-correction image acquisition unit 51.

The structured element designation unit 52 is a processing unit configured to designate a structured element parameter which matches an analysis target. The structured element designation unit 52 calculates the structured element parameter which matches the analysis target from image data of the pre-correction image BP as the analysis target for each of the first image IMG1 and the second image IMG2. The structured element parameter is calculated to have a value corresponding to the size of the analysis target. A configuration of the structured element designation unit 52 and a method for calculating the structured element parameter will be described below.

The correction image generation unit 53 is a processing unit configured to generate and output a correction image CP used to correct image data in image processing, described below. A method for generating the correction image CP will be described below.

Referring to FIG. 1 again, the image processing unit 34 is a processing unit configured to receive as input respective image data of the pre-correction image BP and the correction image CP for each of the first image IMG1 and the second image IMG2 to perform image processing for generating corrected image data, i.e., post-correction image AP.

Figure 3:
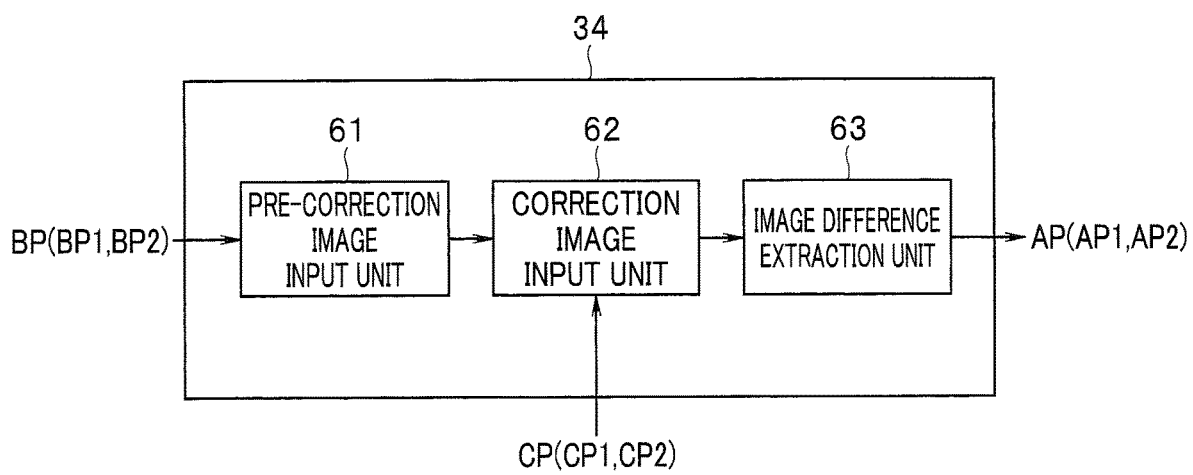
FIG. 3 is a block diagram illustrating a configuration of an image processing unit 34 according to the first embodiment of the present invention.

FIG. 3 is a block diagram illustrating a configuration of the image processing unit 34. The image processing unit 34 includes a pre-correction image input unit 61, a correction image input unit 62, and an image difference extraction unit 63.

The pre-correction image input unit 61 is a processing unit configured to receive as input the pre-correction image BP as an analysis target. A pre-correction image BP1 for the first image IMG1 and a pre-correction image BP2 for the second image IMG2 are outputted from the image input unit 32.

The correction image input unit 62 is a processing unit configured to acquire a correction image CP generated in the correction image generation unit 53. A correction image CP1 for the first image IMG1 and a correction image CP2 for the second image IMG2 are outputted from the signal generation unit 33.

The pre-correction image BP and the correction image CP for each of the first image IMG1 and the second image IMG2 are inputted to the image difference extraction unit 63. The image difference extraction unit 63 takes a difference between the pre-correction image BP and the correction image CP, to extract a difference image and output the difference image as the post-correction image AP. Accordingly, the image difference extraction unit 63 generates a post-correction image AP1 for an analysis target area AA in the first image IMG1 and a post-correction image AP2 for an analysis target area AA in the second image IMG2, and outputs the images to the distribution characteristic value calculation unit 35.

Processing for generating the post-correction image AP in the image processing unit 34 will be described below.

Referring to FIG. 1 again, the distribution characteristic value calculation unit 35 is a processing unit configured to receive as input the post-correction image AP for each of the first image IMG1 and the second image IMG2 and calculate a distribution characteristic value.

Figure 4:
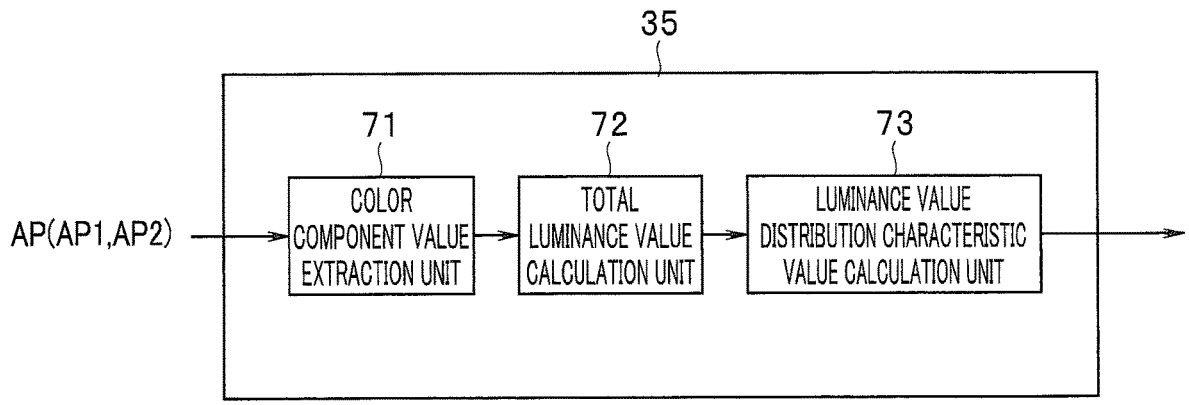
FIG. 4 is a block diagram illustrating a configuration of a distribution characteristic value calculation unit 35 according to the first embodiment of the present invention.

FIG. 4 is a block diagram illustrating a configuration of the distribution characteristic value calculation unit 35. The distribution characteristic value calculation unit 35 includes a color component value extraction unit 71, a total luminance value calculation unit 72, and a luminance value distribution characteristic value calculation unit 73.

The color component value extraction unit 71 extracts each of color component values (an R component value, a G component value, and a B component value) in the post-correction image AP1 for the first image IMG1 outputted from the image difference extraction unit 63 and color component values (an R component value, a G component value, and a B component value) in the post-correction image AP2 for the second image IMG2 outputted from the image difference extraction unit 63.

The total luminance value calculation unit 72 finds a luminance value (first total luminance value) relating to a total value of the color component values in the post-correction image AP1 for the first image IMG1 extracted in the color component value extraction unit 71 while calculating a luminance value (second total luminance value) relating to a total value of the color component values in the post-correction image AP2 for the second image IMG2 extracted in the color component value extraction unit 71.

The luminance value distribution characteristic value calculation unit 73 calculates respective distribution characteristic values (a first distribution characteristic value and a second distribution characteristic value) relating to respective total luminance values (a first total luminance value and a second total luminance value) calculated in the total luminance value calculation unit 37. Note that a "distribution characteristic value" in the present embodiment is found as a standard deviation or a dispersion of a pixel value distribution of a plurality of pixels within the analysis target area AA.

That is, the distribution characteristic value calculation unit 35 extracts the respective color component values in each of the post-correction image AP1 for the first image IMG1 and the post-correction image AP2 for the second image IMG2 which are generated by the image difference extraction unit 63 while calculating a distribution characteristic value of a luminance value relating to a total value of the extracted color component values (details will be described below).

Referring to FIG. 1 again, the image analysis unit 36 calculates a degree of change between the distribution characteristic value (first distribution characteristic value) relating to the post-corrected image AP1 for the first image IMG1 and the distribution characteristic value (second distribution characteristic value) relating to the post-correction image AP2 for the second image IMG2, which have been each calculated in the distribution characteristic value calculation unit 35 respectively (details will be described below).

Then, a configuration of the structured element designation unit 52 will be described.

Figure 5:
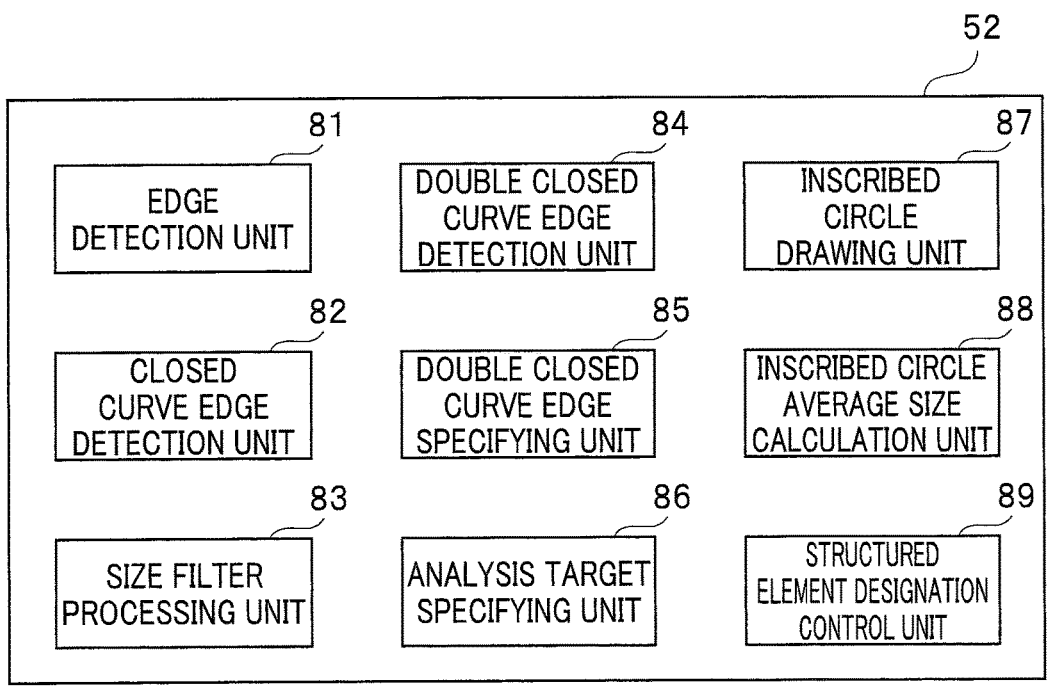
FIG. 5 is a block diagram illustrating a configuration of a structured element designation unit 52 in the signal generation unit 33 according to the first embodiment of the present invention.

FIG. 5 is a block diagram illustrating the configuration of the structured element designation unit 52 in the signal generation unit 33.

The structured element designation unit 52 in the signal generation unit 33 is configured by including an edge detection unit 81, a closed curve edge detection unit 82, a size filter processing unit 83, a double closed curve edge detection unit 84, a double closed curve edge specifying unit 85, an analysis target specifying unit 86, an inscribed circle drawing unit 87, an inscribed circle average size calculation unit 88, and a structured element designation control unit 89, as illustrated in FIG. 5.

The structured element designation unit 52 is a processing unit configured to designate a structured element parameter used when a correction image CP is generated in the correction image generation unit 53 for each of the first image IMG1 and the second image IMG2.

The edge detection unit 81 subjects an image to edge detection filtering, for example, to detect edges.

The closed curve edge detection unit 82 further detects, from among the edges detected by the edge detection unit 81, the edges forming a closed curve.

The size filter processing unit 83 performs processing for selecting, from among the closed curve edges detected by the closed curve edge detection unit 82, only the closed curve edges the size of which is within a range, which can be taken as an element of interest (e.g., within a size range which can be taken as villus in intestinal tract).

The double closed curve edge detection unit 84 detects, from among the closed curve edges detected by the closed curve edge detection unit 82 and further selected by the size filter processing unit 83, for example, the double closed curve edges (i.e., each including an outside closed curve edge and an inside closed curve edge included in the outside closed curve edge).

The double closed curve edge specifying unit 85 specifies, when a color of an area within the inside closed curve edge and a color of an area between the inside closed curve edge and the outside closed curve edge in the double closed curve edge detected by the double closed curve edge detection unit 84 differ from each other, the area within the inside closed curve edge as a central portion.

At this time, the double closed curve edge specifying unit 85 further specifies, when the color of the area in the inside closed curve edge is within a first color range corresponding to a central portion of the element of interest (the first color range is a color range close to red, for example, if the element of interest is the villus in the intestinal tract as an example) and the color of the area between the inside closed curve edge and the outside closed curve edge is within a second color range corresponding to a peripheral portion of the element of interest (a second color range different from the first color range) (the second color range is a color range close to white, for example, if the element of interest is the villus in the intestinal tract as an example), an area in the inside closed curve edge as a central portion.

Note that a color difference is determined based on a difference in at least one of hue, saturation, and luminance as described above. Therefore, a color range becomes a range of at least one of hue, saturation, and luminance or a range determined by a combination of two or more of hue, saturation, and luminance. For example, the color range may be a range determined by a combination of hue and saturation. Alternatively, the color range may be a luminance range (i.e., a central portion and a peripheral portion may be distinguished based on only luminance). If the element of interest is the villus in the intestinal tract and the color range is a luminance range, the first color range may be a range of a slightly low luminance, and the second color range may be a range higher in luminance than the first color range.

Furthermore, the double closed curve edge specifying unit 85 preferably specifies the area in the inside closed curve edge as the central portion only when the size filter processing unit 83 determines that respective sizes of the inside closed curve edge and the outside closed curve edge are within a range which can be taken as the element of interest.

The analysis target specifying unit 86 performs processing for specifying the respective inside closed curve edges in the one or two or more double closed curve edges specified in the double closed curve edge specifying unit 85 as analysis targets.

The inscribed circle drawing unit 87 performs processing for drawing a circle inscribed in each of the analysis targets.

The inscribed circle average size calculation unit 88 performs processing for calculating an average size, here an average value of the respective diameters, of all inscribed circles drawn in the inscribed circle drawing unit 87.

Figure 11:
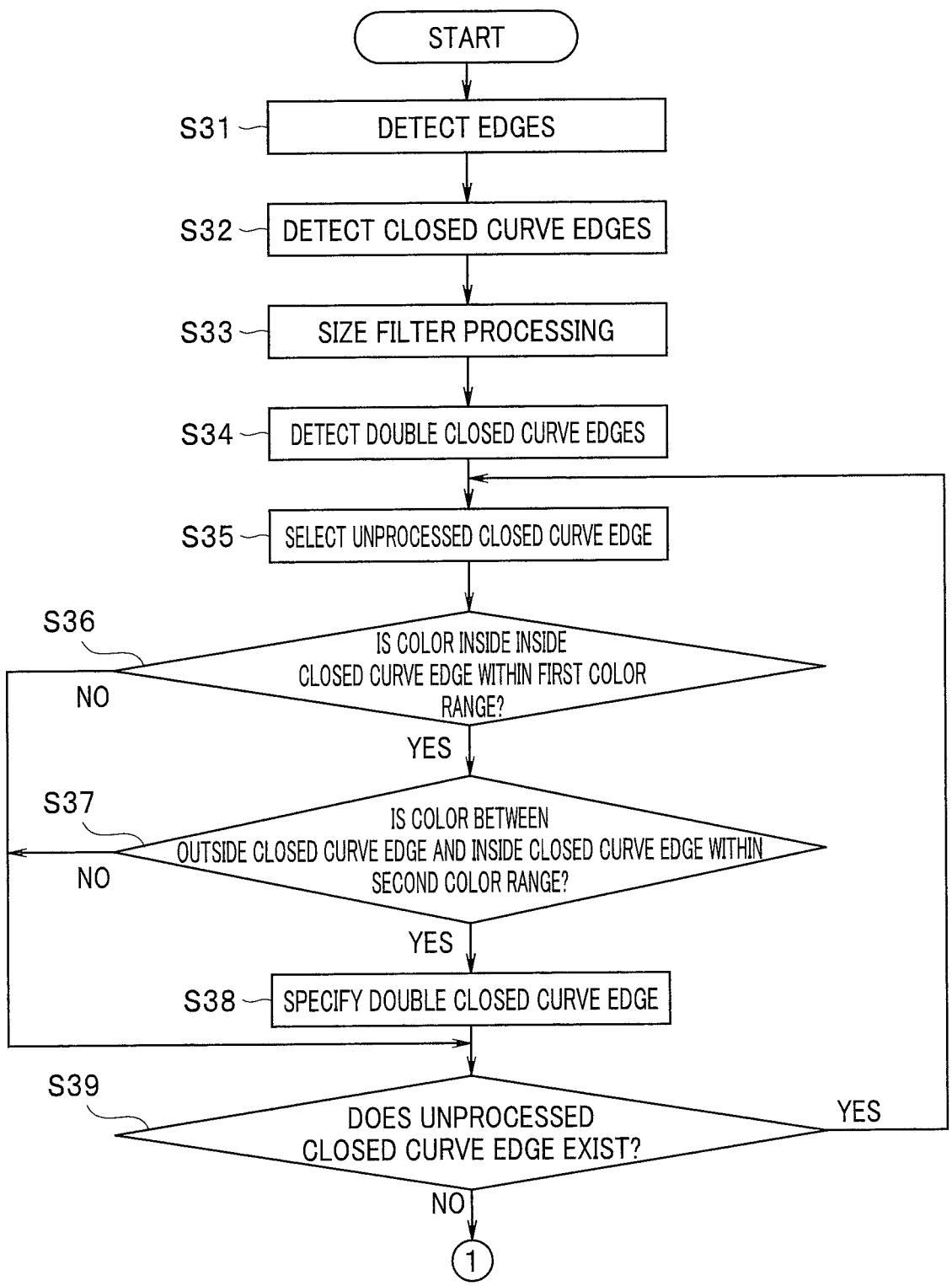
FIG. 11 is a flowchart illustrating an example of a flow of processing for designating a structured element according to the first embodiment of the present invention.
Figure 12:
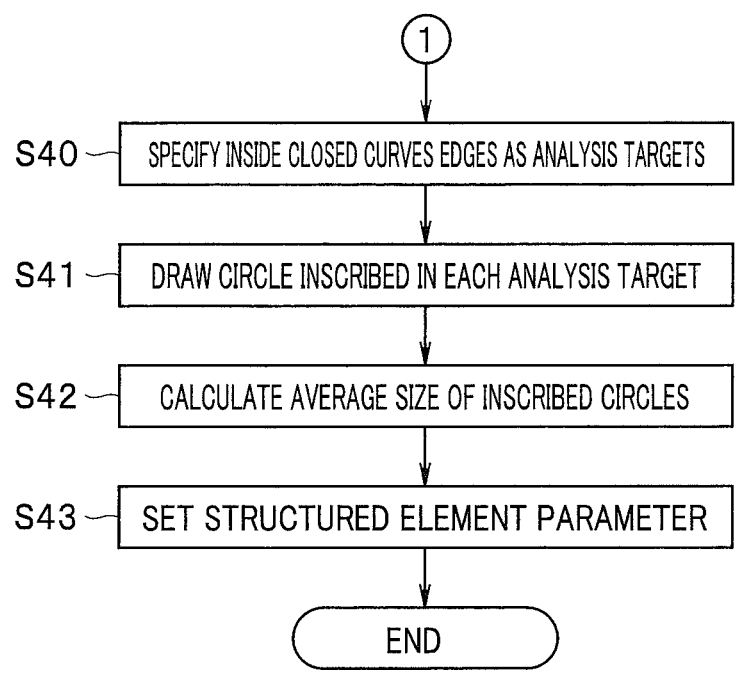
FIG. 12 is a flowchart illustrating an example of a flow of processing for designating a structured element according to the first embodiment of the present invention.

The structured element designation control unit 89 controls the respective units in the structured element designation unit 52, i.e., the edge detection unit 81, the closed curve edge detection unit 82, the size filter processing unit 83, the double closed curve edge detection unit 84, the double closed curve edge specifying unit 85, the analysis target specifying unit 86, the inscribed circle drawing unit 87, and the inscribed circle average size calculation unit 88, described above, to perform an operation as described with reference to FIGS. 11 and 12, described in detail below.

The user as the inspector can apply a predetermined load to a desired body tissue, here villus in small intestine, and detect an amount of change of the body tissue before and after the application of the load by image processing while observing an inside of the subject using the endoscope system 1 having the above-described configuration.

(Function)

An operation of the endoscope system 1 will be described below.

First, an entire flow of processing of the endoscope system 1 when the user mounts the distal end hood on the distal end portion of the insertion section to set the endoscope system 1 to a narrow band imaging (NBI) mode and observes villus in the small intestine in an enlarged manner will be described.

<Entire Flow>

The user can observe a change of a subject in real time by applying a predetermined load (function) to a desired site while observing an inside of the small intestine in an enlarged manner using the endoscope system 1.

The user can use the endoscope system 1 to estimate a state of the subject, for example, by previously storing a change of the subject when a predetermined load is applied to a plurality of normal tissues or a change of the subject when a predetermined load is applied to a diseased tissue as a reference sample in a storage device and comparing a change of a subject to be inspected when the same predetermined load is applied to the subject with the reference sample.

Therefore, in the endoscope system 1, image data corresponding to a plurality of consecutive frames are acquired, and changes of the subject before and after the function is applied are detected from respective color components in two endoscope images determined in response to an instruction from the user.

First, a relationship between a flow of processing for detecting a change of a subject and an image will be described.

Figure 6:
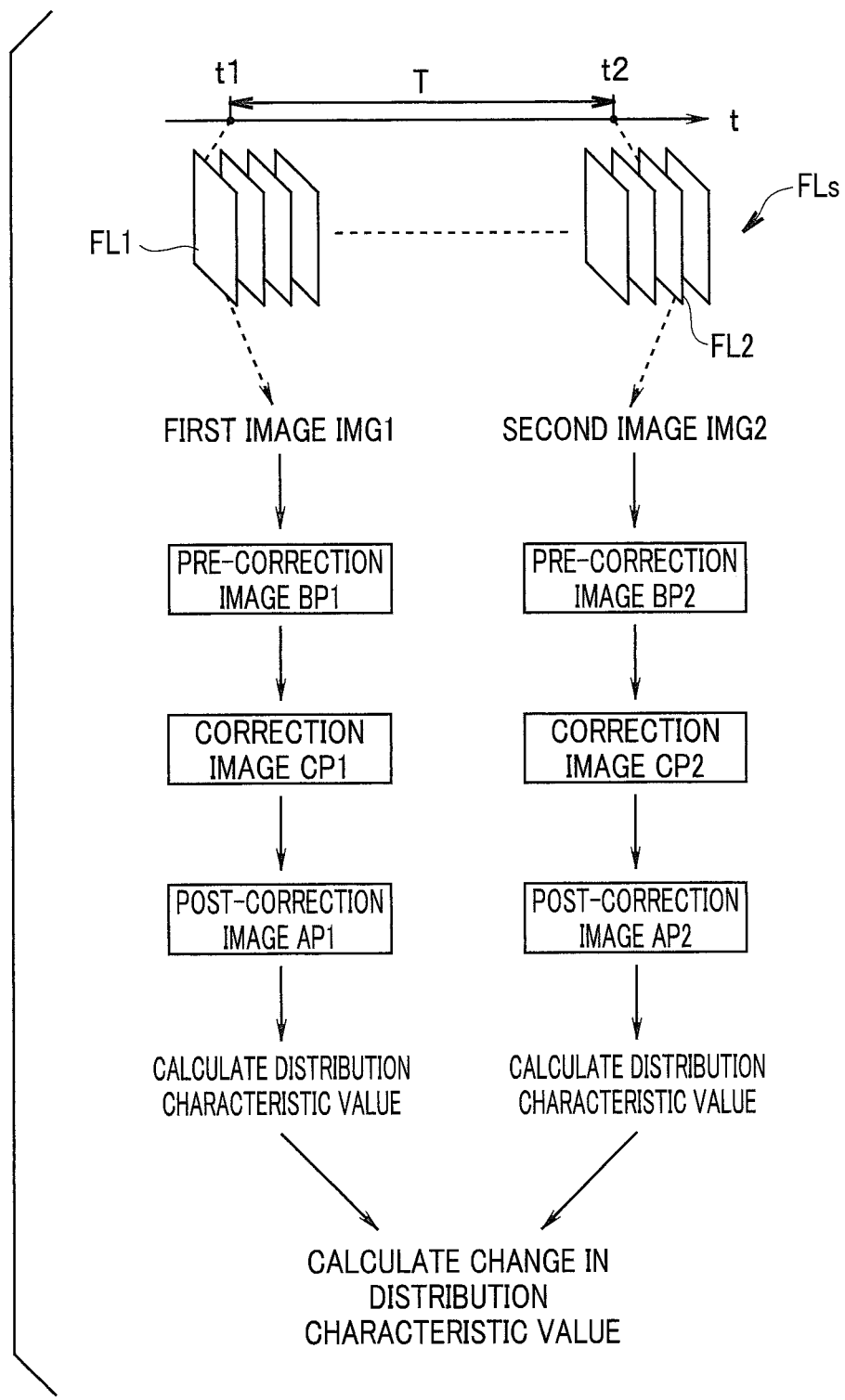
FIG. 6 is a diagram for illustrating a flow of processing for detecting a change of a subject from acquired two endoscope images according to the first embodiment of the present invention.

FIG. 6 is a diagram for describing the flow of processing for detecting a change of a subject from acquired two endoscope images.

As described above, a first image IMG1 of the subject before a predetermined load is applied and a second image IMG2 of the subject after the predetermined load is applied are acquired. As the acquired first image IMG1 and second image IMG2, an image including no wide halation area is selected.

In FIG. 6, among a plurality of frames FLs obtained during inspection, a frame FL1 acquired at a first timing t1 before a predetermined load is applied to the subject is a first image IMG1, and a frame FL2 acquired at a second timing t2 of when a predetermined time period T has elapsed after the predetermined load is applied to the subject is a second image IMG2.

The image input unit 32 receives as input and acquires the first image IMG1 of the subject acquired at the first timing t1 before the predetermined function is applied to the subject and the second image IMG2 of the subject acquired at the second timing t2 after the function is applied to the subject later than the first timing t1 by the endoscope 2 continuously inserted into the subject.

Analysis target areas AA extracted from the acquired first image IMG1 and second image IMG2 are respectively extracted as pre-correction images BP1 and BP2.

Correction images CP1 and CP2 are respectively generated from the pre-correction images BP1 and BP2. A correction image CP is brightness distribution correction data for correcting a brightness distribution in which brightness has an overall slope to suppress an optical influence on color components composing a pre-correction image BP.

The above described signal generation unit 33 generates the correction image CP1 as first brightness distribution correction data for correcting a brightness distribution in which brightness has an overall slope of the first image IMG1 to suppress an optical influence on color components composing the first image IMG1 using the first image IMG1 as a pre-correction image while generating a correction image CP2 as second brightness distribution correction data for correcting a brightness distribution in which brightness has an overall slope of the second image IMG2 to suppress an optical influence on color components composing the second image IMG2 using the second image IMG2 as a pre-correction image.

That is, the signal generation unit 33 constitutes a correction data generation section configured to generate the first brightness distribution correction data for correcting the slope of the brightness distribution of the inputted first image IMG1 using the first image IMG1 while generating the second brightness distribution correction data for correcting the slope of the brightness distribution for the second image IMG2 using the second image IMG2.

Post-correction images AP1 and AP2 are respectively generated from the pre-correction images BP1 and BP2 and the correction images CP1 and CP2. The generated post-correction images AP1 and AP2 are each an image a brightness distribution of which is not affected by a light distribution characteristic of illumination, a slope of a surface of an object to an optical axis of an observation optical system, a distance from the distal end portion of the insertion section to an observation target, non-flatness of the surface of the object, or the like.

The above-described image processing unit 34 generates the post-correction image AP1 as a first processed image obtained by causing the correction image CP1 as the first brightness distribution correction data to act on the first image IMG1 and the post-correction image AP2 as a second processed image obtained by causing the correction image CP2 as the second brightness distribution correction data to act on the second image IMG2.

For each of the post-correction image AP1 and the post-correction image AP2, a distribution characteristic value is calculated. The distribution characteristic value calculation unit 35 extracts color components in the post-correction image AP1 as the first processed image to find a first distribution characteristic value while extracting color components in the post-correction image AP2 as the second processed image to find a second distribution characteristic value.

When an amount of change from the calculated distribution characteristic value for the post-correction image AP1 to the calculated distribution characteristic value for the post-correction image AP2 is calculated, a change of the subject when the predetermined load is applied to the subject can be quantitatively determined, and can be compared with the reference sample previously acquired. The image analysis unit 36 calculates a degree of change of the second distribution characteristic value for the post-correction image AP2 from the first distribution characteristic value for the post-correction image AP1.

Note that the subject is the villus in the small intestine existing on an inner surface of the intestinal tract of a living body, for example, in the present embodiment, the subject is not limited to the villus in the small intestine, but may be tongue, esophagus, gastric mucosa, large intestine, and the like as some other examples.

Then, processing from acquisition of an image to analysis of the image in the video processor 3 will be described.

Figure 7:
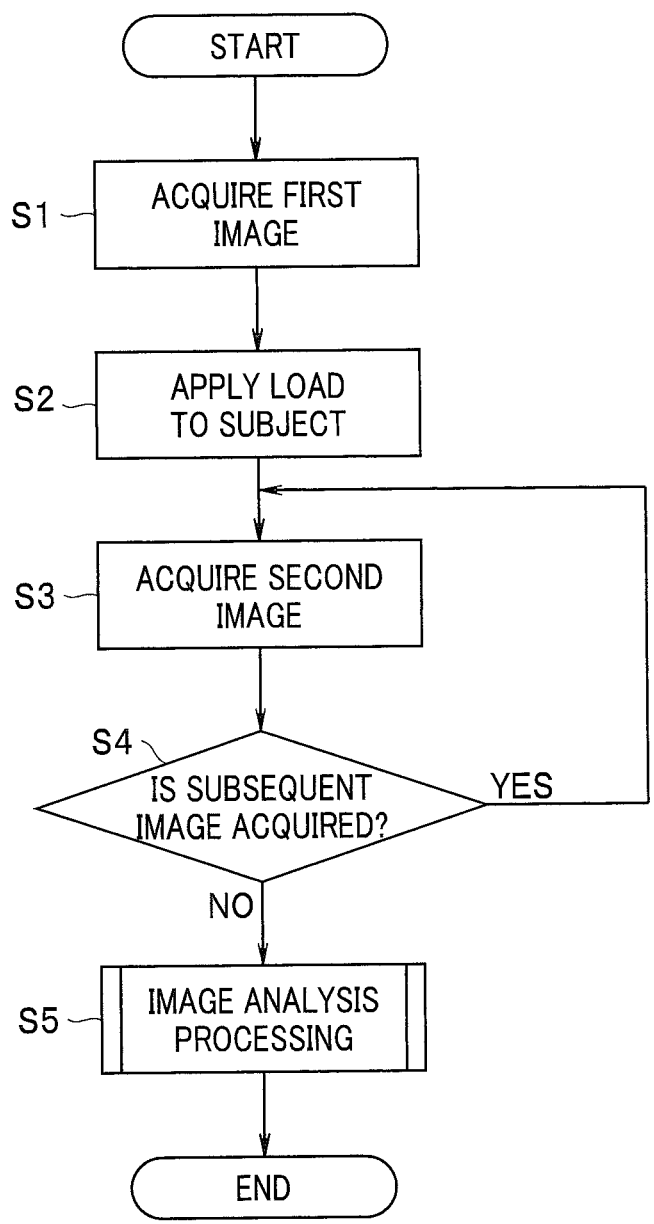
FIG. 7 is a flowchart illustrating basic processing for detecting a change of a subject from color components composing image data of an endoscope image according to the first embodiment of the present invention.

FIG. 7 is a flowchart illustrating basic processing for detecting a change of a subject from color components composing image data of an endoscope image.

The user uses the endoscope system 1, to observe the endoscope image within the subject while displaying the endoscope image within the subject on the display apparatus 5.

Here, the user sets the endoscope system 1 to an enlarged observation mode by NBI to observe the inside of the subject while displaying the endoscope image by NBI on the display apparatus 5. The endoscope image obtained during the observation is stored in a large-capacity storage device such as a hard disk device (not illustrated).

The control unit 31 first controls the endoscope 2, to acquire an image before a load (predetermined function) is applied to the subject (a first image IMG1 as a pre-load image) from the image pickup unit 11 at a first timing t1 (step S1). The first image IMG1 is acquired in response to an operation of the release button by the user, for example.

When the first image IMG1 is acquired, the control unit 31 controls the image input unit 32 to receive as input an image signal from the endoscope 2 and store the inputted image signal in the memory 32a. The memory 32a also stores endoscope images respectively corresponding to a plurality of frames acquired after the time when the acquired first image IMG1 is acquired.

At the same time that the image of the subject is acquired by the endoscope 2, information about an amount of emitted light at the time when the image is acquired may be recorded in the image analysis apparatus (video processor 3) or the endoscope 2, for example.

The user determines an area of a living tissue, to which a load is to be applied, of the subject to be displayed on the display apparatus 5 while observing an enlarged observation image by NBI of the subject, and applies the load (predetermined function) to the subject (step S2). The load (predetermined function) to the subject in step S2 is spraying of glucose. When glucose is sprayed, an amount of blood flowing through capillaries increases, and more light is absorbed by hemoglobin in the blood. Therefore, a portion where the capillaries are gathered within the villus is observed to be dark.

For example, glucose is sprayed, by a predetermined instrument being inserted through a treatment instrument insertion channel of the endoscope 2, to a surface of the subject from a distal end of the instrument projecting from the distal end portion of the insertion section.

Note that the load (predetermined function) to the subject is not limited to the load but may be administration of a medicinal solution to the subject, for example, normal saline, glucose, or liquid fat (fat emulsion, etc.), as described above, and further is not limited to administration of a medicinal solution but may be a function such as intravenous injection, air feeding into a body cavity, or physical contact of a treatment instrument or an endoscope itself with an inside of a body, for example.

Then, the control unit 31 applies the load to the subject with the endoscope 2 continuously inserted into the subject, and then acquires a second image IMG2 from the endoscope 2 (step S3). The control unit 31 acquires the first image IMG1, and then continuously acquires image data corresponding to a plurality of frames FLs for a predetermined time period T, to acquire image data of an image corresponding to the frame FL2 when the predetermined time period T has elapsed as image data of the second image IMG2.

Note that when glucose is administered to the subject as an example of the function in the present embodiment, the predetermined time period T is a period of approximately three minutes (180 seconds) after the function.

The control unit 31 further determines whether the subsequent image is acquired (step S4). If it is determined that the subsequent image is acquired, the processing returns to step S3. In step S3, the control unit 31 acquires a subsequent post-load image. That is, after the first image IMG1 is acquired, the subsequent image is acquired until the predetermined time period T elapses. When the predetermined time period T elapses, the control unit 31 acquires the image data of the image corresponding to the frame FL2 at the time when the predetermined time period has elapsed as the image data of the second image IMG2, and the processing proceeds to step S5.

If it is determined that the acquisition of the image has ended in step S4, the control unit 31 controls the signal generation unit 33, the image processing unit 34, the distribution characteristic value calculation unit 35, the image analysis unit 36, and the like in the video processor 3, to perform image analysis (step S5). After the image analysis is completed, the processing ends.

Here, when the image after the load is applied to the subject is acquired from the endoscope 2, if the information about the amount of emitted light is recorded in step S1, the image is acquired under the same condition as the condition in step S1 while referring to the information about the amount of emitted light. Note that the control unit 31 may have a function of erasing information about the amount of emitted light, which has been recorded in step S1, later. Acquisition of the information about the amount of emitted light, acquisition of the image using the information about the amount of emitted light, and erasure of the information about the amount of emitted light may be implemented by respective operations of the operation section in the endoscope 2, a switch provided in a control panel for controlling the image analysis system, or a foot switch for operating the endoscope 2, for example.

As described above, the endoscope system 1 extracts from among image data of a plurality of images stored in the image input unit 32 the image data before and after the load (predetermined function) is applied to the subject, and performs predetermined image analysis processing for the extracted image data (step S5).

Accordingly, the user can apply the load to the subject while performing endoscope observation in real time and see respective states of changes of the subject before and after the load is applied.

<Flow of Image Analysis>

Then, a flow of the image analysis processing in step S5 will be described.

Figure 8:
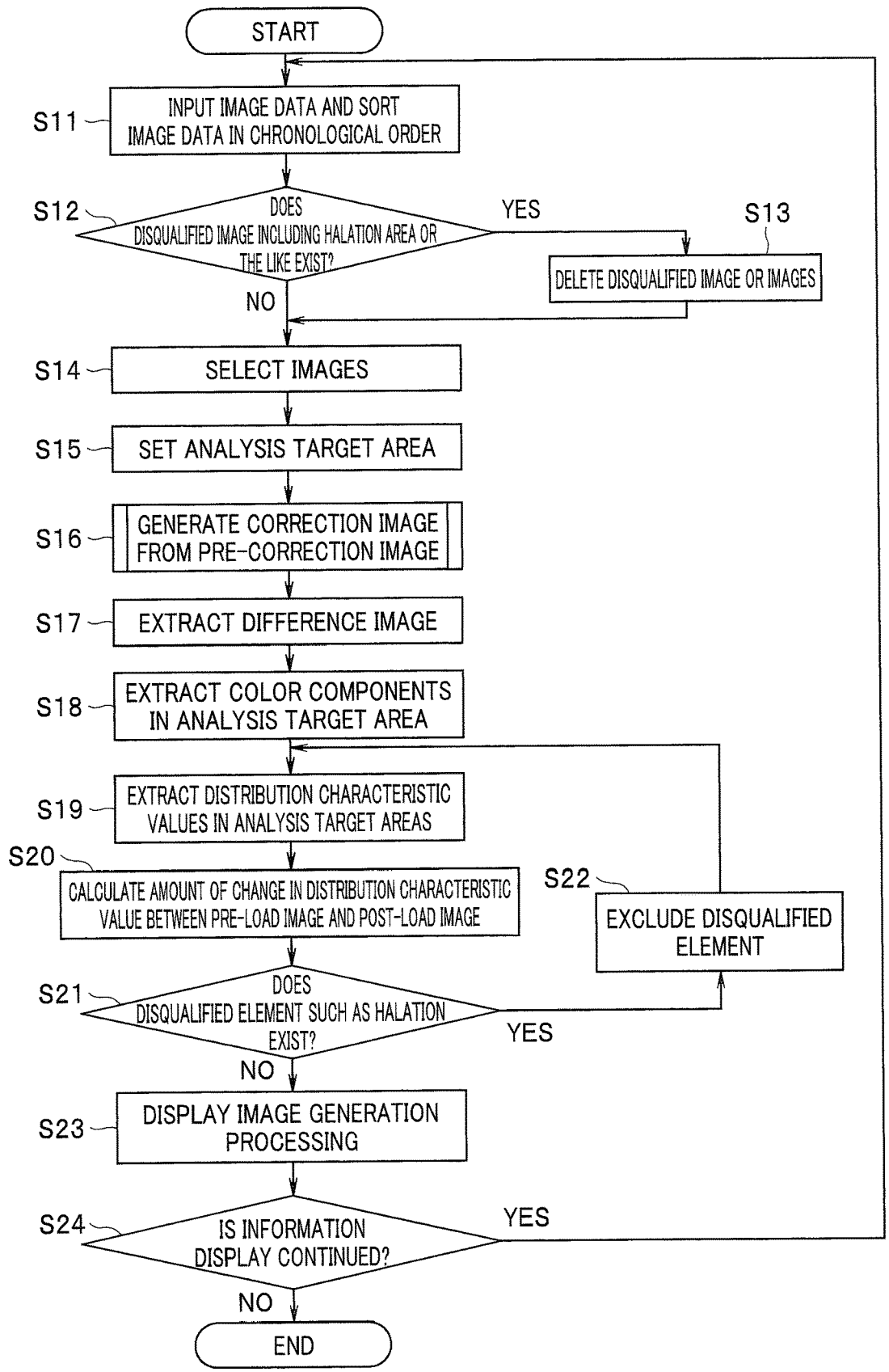
FIG. 8 is a flowchart illustrating image analysis processing by a video processor 3 as an image analysis apparatus in the image analysis system according to the first embodiment of the present invention.

FIG. 8 is a flowchart illustrating image analysis processing by the video processor 3 as the image analysis apparatus in the image analysis system according to the first embodiment.

When the processing is started under control of the control unit 31, the image input unit 32 sorts image data of the subject time-sequentially acquired from the endoscope 2 and stored in the memory 32a in chronological order (step S11).

The image data inputted to the image input unit 32 are respectively image data corresponding to a plurality of frames from the first image IMG1 before the load (predetermined function) is applied to the subject until after a lapse of a predetermined time period T since the load was applied to the subject.

The image input unit 32 determines whether a frame corresponding to a disqualified image including a wide halation area or the like exists among the sorted image data corresponding to the plurality of frames (step S12). When a pixel value is a value within a range from 0 to 255 and when a pixel area where the pixel value is 230 or more using 230, for example, as a threshold value, occupies a predetermined proportion or more in a frame, the frame is determined to correspond to a disqualified image. That is, the image input unit 32 determines whether each of the plurality of image, which have been sorted in step S11, is a disqualified image unsuited to extract color component values. When a predetermined number or more of pixels respective luminance values of which are a predetermined value or more exist in the image data corresponding to one frame, an image corresponding to the frame is determined as a disqualified image because the image includes a wide halation area. Examples of a disqualified area include an area where air bubbles occur and an area where a defocus occurs in addition to an area where halation occurs.

When the disqualified image exists among the image data corresponding to the plurality of frames (step S12: YES), the image input unit 32 deletes the image data corresponding to one or two or more frames, which have been each determined to correspond to a disqualified image, from among the image data corresponding to the plurality of frames which have been obtained in step S11 (step S13).

Note that the image input unit 32 compares a pixel value of each of the pixels in each of the frames and a predetermined value as a predetermined threshold value with each other, to determine that the image in the frame is a disqualified image when the size of the halation area or the like in the frame is the predetermined value or more, the user may be made to determine that the image in the frame is a disqualified image. The user may be made to determine, by displaying the image in the frame where the halation area or the like has a size equal to or more than a predetermined value on a screen of the display apparatus 5, whether the image in the frame is a disqualified image and delete the disqualified image in frame units.

Figure 9:
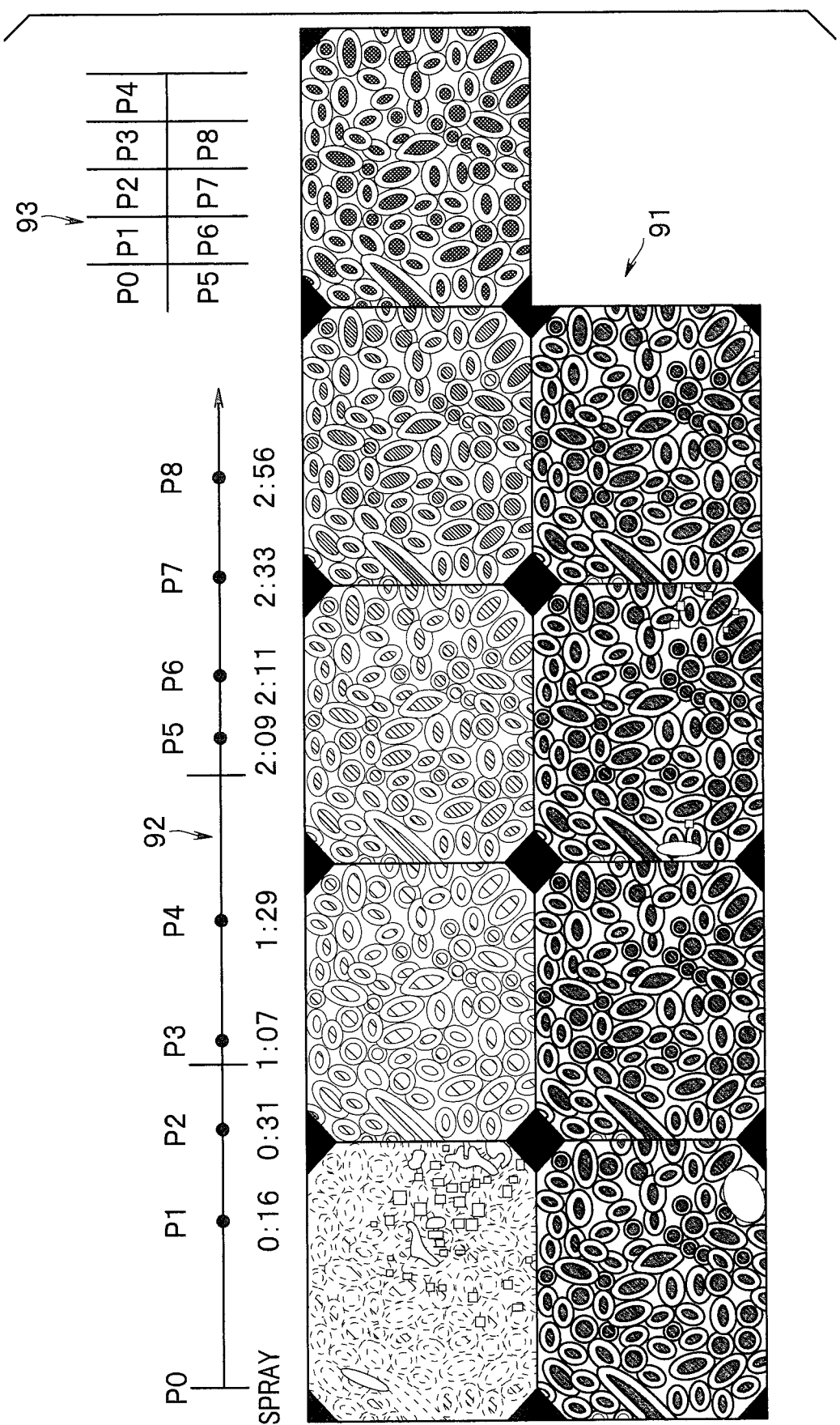
FIG. 9 is a diagram illustrating an example of images of a subject sorted in chronological order according to the first embodiment of the present invention.

FIG. 9 is a diagram illustrating an example of images of a subject sorted in chronological order.

Note that on image arrangement display 91 illustrated in FIG. 9, only images P0 to P8 among the sorted images are displayed in the order of time in which the images are acquired. At an acquisition timing of each of the images is displayed on image acquisition time display 92. On the image acquisition time display 92, a time point where each of the images P1 to P8 has been acquired after a load is applied (glucose is sprayed in the present embodiment), together with an acquisition time, is displayed along a time axis, for example. A correspondence relationship between each of the images P0 to P8 and the acquisition timing is displayed on image arrangement order display 93.

Accordingly, in the image input unit 32, image data corresponding to a plurality of frames from the image P0 (the first image IMG1) immediately before a load is applied until after a lapse of a predetermined time period T since the load was applied are acquired and stored in the memory 32*a*, and the frame corresponding to a disqualified image is deleted from among the plurality of frames in step S13.

Note that although the image P0 is the first image IMG1 acquired before glucose is sprayed (e.g., immediately before glucose is sprayed), the image P0 is displayed at a position where glucose is sprayed for convenience in FIG. 9 (the time axis may be extended to a time point before glucose is sprayed to accurately display a time point where the image P0 is acquired).

Referring to FIG. 8 again, the image input unit 32 performs image selection for selecting and acquiring the two images to be analyzed from among the image data corresponding to the plurality of frames each including no disqualified image and outputs the images to the signal generation unit 33 (step S14) after step S12 or step S13. That is, the image input unit 32 selects, from among the images of the subject acquired from the endoscope 2, the first image IMG1 and the second image IMG2 except for the image including a predetermined number or more of disqualified elements each unsuited to extract color component values.

The two images are the first image IMG1 and the second image IMG2 at a timing of when the predetermined time period T has elapsed or when the predetermined time period T has not elapsed from the acquisition timing of the first image IMG1.

The signal generation unit 33 sets an analysis target area AA for each of the acquired images (step S15). The pre-correction image acquisition unit 51 in the signal generation unit 33 acquires the two images (the first image IMG1 and the second image IMG2) to be analyzed, and sets the analysis target area for each of the images. In a process in step S15, an analysis target area setting section is configured to set the analysis target area AA in each of the first image IMG1 and the second image IMG2.

Figure 10:
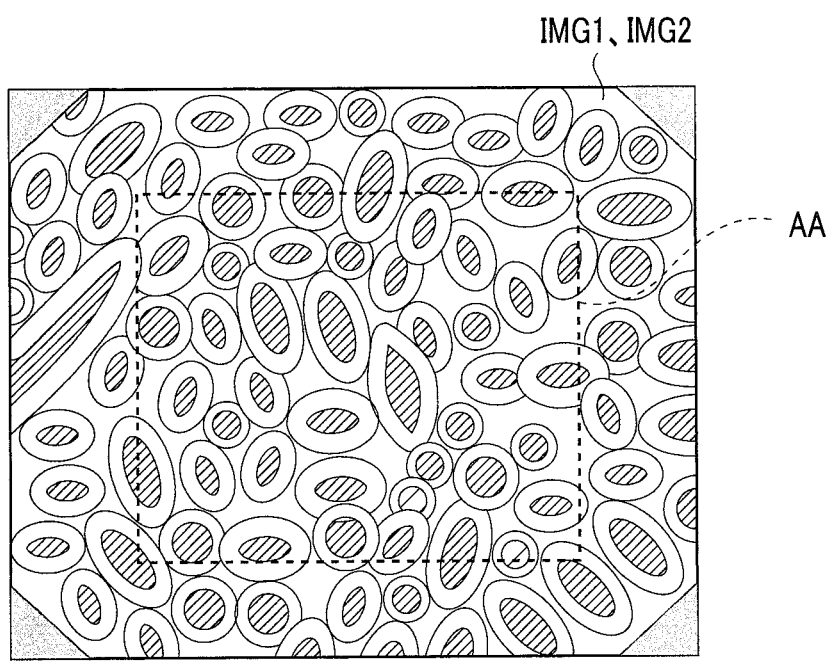
FIG. 10 is a diagram for describing an analysis target area AA in an image according to the first embodiment of the present invention.

FIG. 10 is a diagram for describing an analysis target area AA in an image.

The analysis target area AA is previously set in each of a first image IMG1 and a second image IMG2 as a pixel area where color components are accurately extracted. The analysis target area AA may be set by the user or may be previously set in the endoscope system 1.

Here, the analysis target area AA is a rectangular area around the center, which is in focus, of an endoscope image, and is an area where the image is less distorted. If the user sets the analysis target area AA in the image, a condition that the analysis target area AA is an area where brightness is as uniform as possible and an area where no or little halation exists in addition to a selection condition that the analysis target area AA is an area which is in focus and an area where the image is less distorted.

Note that although the one analysis target area AA is set for each of the first image IMG1 and the second image IMG2 in FIG. 10, a plurality of analysis target areas AA may be set in each of the first image IMG1 and the second image IMG2.

The signal generation unit 33 generates a correction image CP from a pre-correction image BP (step S16).

The pre-correction image BP is for each of the first image IMG1 and the second image IMG2, and is acquired in the pre-correction image acquisition unit 51. In the signal generation unit 33 functioning as a correction data generation section, the correction image CP is generated for each of the first image IMG1 and the second image IMG2.

The structured element designation unit 52 designates a structured element, which matches each of the first image IMG1 and the second image IMG2 to be analyzed, and the correction image generation unit 53 generates the correction image CP for each of the first image IMG1 and the second image IMG2 using a designated structured element parameter.

More specifically, the signal generation unit 33 extracts respective pluralities of areas, each surrounded by a closed curve, from the first image IMG1 and the second image IMG2 by functioning as the correction data generation section, and respectively generates correction images CP1 and CP2 as brightness distribution correction data based on an average size of respective inscribed circles of the extracted areas.

Note that when the plurality of analysis target areas AA are set in each of the first image IMG1 and the second image IMG2, the signal generation unit 33 generates the correction image CP1 as first brightness distribution correction data and the correction image CP2 as second brightness distribution correction data for each of the analysis target areas AA set in each of the first image IMG1 and the second image IMG2 by functioning as the correction data generation section.

(Processing for Designating Structured Element)

First, processing for designating a structured element in the structured element designation unit 52 will be described.

FIGS. 11 and 12 are each a flowchart illustrating an example of a flow of the processing for designating the structured element.

The structured element designation unit 52 has the configuration illustrated in FIG. 5, as described above. The edge detection unit 81 subjects the analysis target area AA to edge detection filtering, to extract edge components and detect edges (step S31).

Then, the closed curve edge detection unit 82 further detects the edges each forming a closed curve from among the edges detected by the edge detection unit 81 (step S32).

Then, the size filter processing unit 83 calculates the size of the closed curve edge detected by the closed curve edge detection unit 82 (e.g., a maximum diameter and an average diameter of the closed curve or the area of an area surrounded by the closed curve), and selects only the closed curve edges the respective calculated sizes of which are each within a range which can be taken as an element of interest (e.g., within a range which can be taken as the villus in the intestinal tract) (step S33).

The double closed curve edge detection unit 84 detects all double closed curve edges from among the closed curve edges which have passed through the size filter processing unit 83 (step S34).

Note that both the inside closed curve edge and the outside closed curve edge, which constitute the double closed curve edge, are each a closed curve edge which has been determined to have a size within the range which can be taken as the element of interest because the edges have passed through the size filter processing unit 83 in step S33.

Furthermore, the double closed curve edge specifying unit 85 selects one of the plurality of double closed curve edges detected by the double closed curve edge detection unit 84 (step S35), and determines whether a color inside the inside closed curve edge, e.g., an average value of color component values of each of pixels is within a first color range corresponding to a central portion of the element of interest (step S36).

Here, if it is determined that the color inside the inside closed curve edge is outside a first color range, the double closed curve edge, which has been selected in step S36, is not identified as the element of interest, and the processing proceeds to step S39.

If it is determined that the color inside the inside closed curve edge is within the first color range (YES in step S36), the double closed curve edge specifying unit 85 further determines whether the color between the outside closed curve edge and the inside closed curve edge in the selected double closed curve edge, e.g., the average value of the color component values of each of the pixels is within a second color range corresponding to a peripheral portion of the element of interest (step S37).

If it is determined that the color between the outside closed curve edge and the inside closed curve edge in the selected double closed curve edge is within the second color range (YES in step S37), the double closed curve edge specifying unit 85 specifies the double closed curve edge, which has been selected in step S35, as an element of interest (step S38).

Here, if it is determined that the color between the outside closed curve edge and the inside closed curve edge is outside the second color range, the double closed curve edge, which has been selected in step S35, is not identified as an element of interest, and the processing proceeds to step S39.

After step S38, the structured element designation control unit 89 determines whether among a plurality of double closed curve edges detected by the double closed curve edge detection unit 84, the unprocessed double closed curve edge, which has not been subjected to respective processes in steps S36 to S38 yet, exists (step S39). If the unprocessed double closed curve edge exists, the processing returns to step S35, and a process in step S35 is performed for the subsequent double closed curve edge.

If it is thus determined that the process in step S35 and the subsequent steps have been performed for all the double closed curve edges (NO in step S39), the analysis target specifying unit 86 specifies the inside closed curve edge in each of the one or two or more double closed curve edges, which have been specified in step S38, as an analysis target (step S40).

The inscribed circle drawing unit 87 draws an inscribed circle of each of the analysis targets (step S41).

The inscribed circle average size calculation unit 88 calculates an average size, here an average value of diameters of all the inscribed circles which have been drawn in step S41 (step S42).

A value corresponding to the average size, which has been calculated in step S42, is set as a structured element parameter (step S43).

Significance of a specific structured element parameter will be described with reference to FIGS. 13 and 14.

Figure 13:
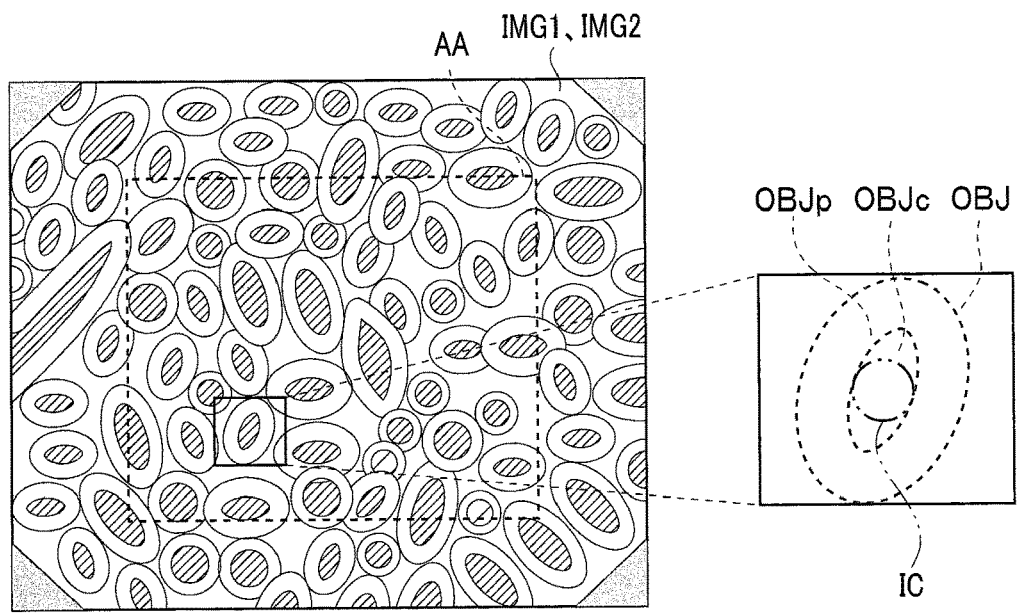
FIG. 13 is a diagram illustrating an endoscope image of a subject and one of elements of interest in an enlarged manner according to the first embodiment of the present invention.

FIG. 13 is a diagram illustrating an endoscope image of a subject and one of elements of interest in an enlarged manner. FIG. 14 is a diagram illustrating a structure of the villus in the intestinal tract as the element of interest.

Although the double closed curve edge is specified as an element of interest in step S35 in each of the first image IMG1 and the second image IMG2 illustrated in FIG. 13, for example, one double closed curve corresponds to one villus in the intestinal tract.

Figure 14:
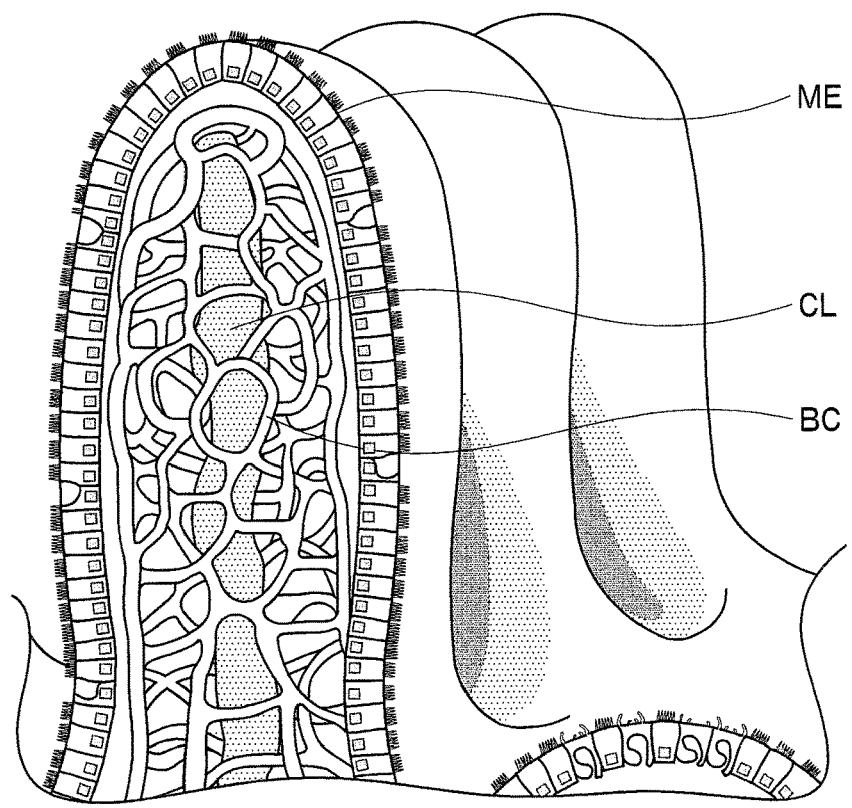
FIG. 14 is a diagram illustrating a structure of villus in intestinal tract as an element of interest according to the first embodiment of the present invention.

As illustrated in FIG. 14, the villus in the intestinal tract has a structure in which capillaries BC are distributed in a site around a central lymph channel CL in the central portion and mucosal epithelium ME is formed outside the capillaries to constitute a surface of the villus.

When the villus in the intestinal tract is observed in an enlarged manner by NBI using light having a band-narrowed wavelength, which is easily absorbed in hemoglobin in blood, a portion of the capillaries BC is observed as a color different from the color of the mucosal epithelium ME.

When an image portion obtained by picking up the villus from above is observed, an image portion of the mucosal epithelium ME is observed as an annular peripheral portion OBJp, and an image portion of the capillaries BC surrounded by the mucosal epithelium ME is observed as a central portion OBJc different in color from the mucosal epithelium ME. Accordingly, an element of interest OBJ is determined using a difference in color between the central portion OBJc and the peripheral portion OBJP, as described above.

The inside closed curve edge in each of the double closed curve edges is set as an analysis target in step S40, described above, and an inscribed circle of each of the inside closed curve edge is drawn in step S41. In FIG. 13, a circle indicated by a two-dot and dash line is an inscribed circle IC of the inside closed curve edge drawn in step S41. If a shape of an image of the central portion OBJc, corresponding to the capillaries BC, of the villus in the small intestine is a shape of an ellipse, for example, the diameter of the inscribed circle IC becomes a length of a short axis of the ellipse.

Furthermore, an average size of all the inscribed circles IC is calculated in step S42, and the calculated average size is set as a structured element parameter in step S43. That is, the structured element parameter is a value corresponding to the size of the analysis target.

Note that although the structured element designation unit 52 determines the structured element parameter based on each of the first image IMG1 and the second image IMG2 to be analyzed, a previously set value PP may be set as a structured element parameter, as indicated by a dotted line in FIG. 2.

For example, the value PP used in enlarged observation of the villus in the small intestine may be set as the structured element parameter by being previously designated. The size of the villus in the small intestine as an object changes depending on a distance between the object and the distal end portion of the insertion section. Thus, a plurality of values PP may be previously prepared depending on the distance, and the user may select a value corresponding to the distance when image analysis is performed.

The structured element obtained in the above-described manner is an optimum parameter value to detect a color change of the villus in the small intestine to be analyzed. Here, the structured element is set to a value not exceeding an average value of the diameters of the inscribed circles IC of the inside closed curve edges to be analyzed.

Furthermore, the structured element parameter is calculated and found from an image to be analyzed here. Thus, even if a distance between the distal end portion of the insertion section of the endoscope 2 and the object changes, the structured element is determined in real time for an image a color change of which is to be detected.

Note that the structured element has a circular shape including a plurality of pixels centered around a pixel of interest here, a shape in a range where the structured element is defined may be a shape other than a circle, or may be changed depending on an analysis target.

(Processing for Generating Correction Image)

Processing for generating a correction image in the correction image generation unit 53 will be described below.

In step 16 illustrated in FIG. 8, the correction image CP is generated using the structured element parameter designated in the structured element designation unit 52.

The correction image generation unit 53 performs image processing, described below, to generate the correction image CP for each of the pre-correction image BP1 for the first image IMG1 and the pre-correction image BP2 for the second image IMG2.

Figure 15:
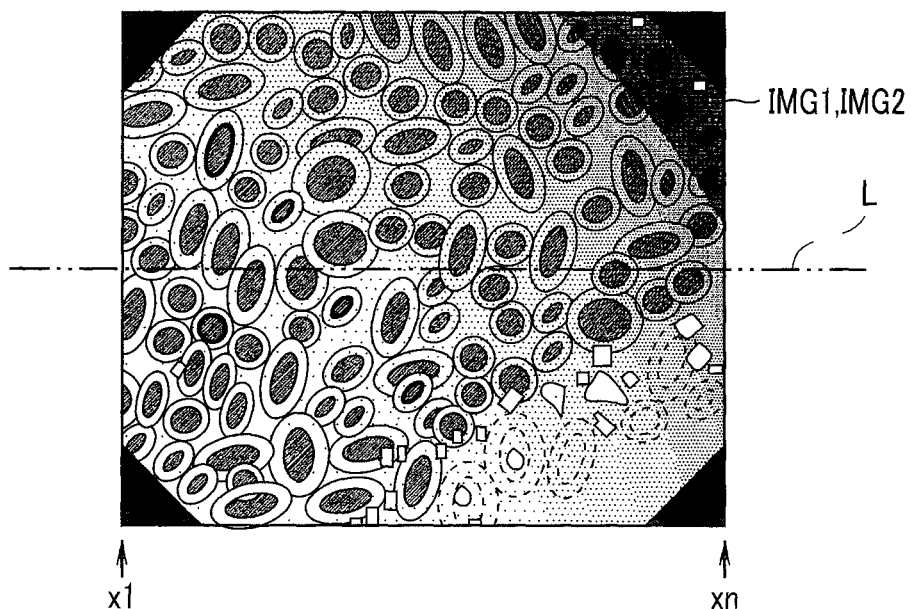
FIG. 15 is a diagram illustrating an example of an endoscope image according to the first embodiment of the present invention.
Figure 16:
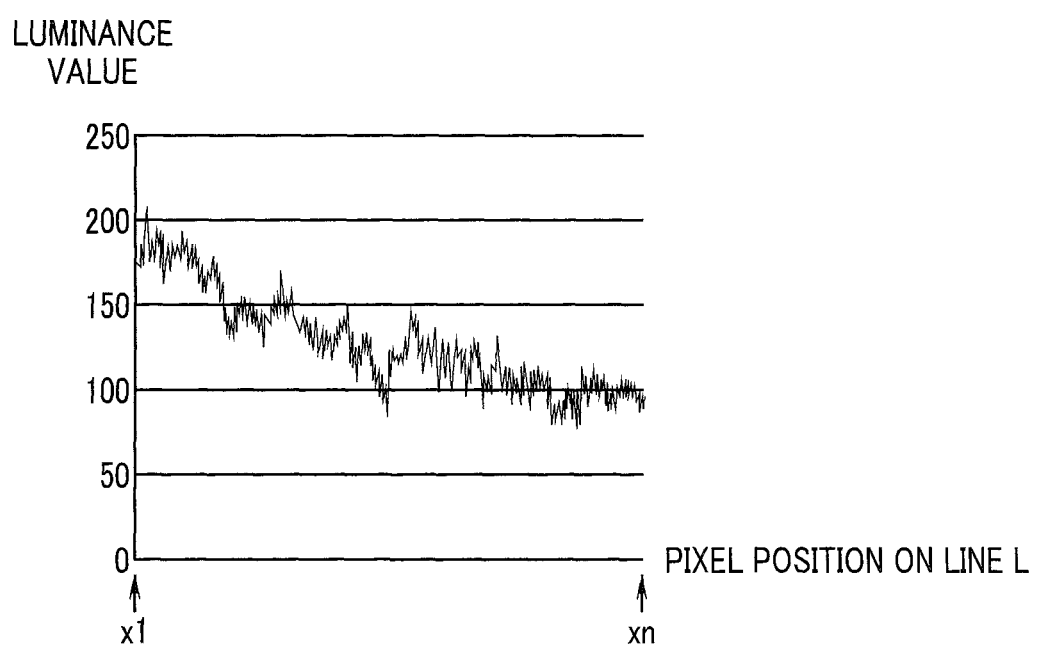
FIG. 16 is a graph illustrating a luminance distribution of a pixel group on a line L indicated by a two-dot and dash line within an analysis target area AA in the endoscope image illustrated in FIG. 15.

FIG. 15 is a diagram illustrating an example of an endoscope image. FIG. 16 is a graph illustrating a luminance distribution of a pixel group on a line L indicated by a two-dot and dash line within an analysis target area AA in the endoscope image illustrated in FIG. 15. FIG. 16 illustrates a luminance distribution of a pixel group in a range from a pixel x1 to a pixel xn on the line L in the endoscope image.

The endoscope image illustrated in FIG. 15 has such a brightness distribution that brightness decreases from the lower left portion to the upper right portion. Consequently, a luminance value of the pixel group on the line L is high on the left side and is low on the right side, as illustrated in FIG. 16.

When a change of a subject is detected from color components in an endoscope image a brightness distribution of which is affected by a light distribution characteristic of illumination or a slope of a surface of an object to an optical axis of an observation optical system, for example, a luminance value of each of pixels is affected by the brightness distribution. Thus, the change of the subject is difficult to accurately be detected.

If the change of the subject is detected based on a value such as a standard deviation or a dispersion of respective luminance values of color components in the endoscope image, the brightness distribution of the endoscope image changes due to an influence of the light distribution characteristic of the illumination, for example. Thus, the change is difficult to be accurately detected.

In the present embodiment, the pre-correction image BP is corrected by performing predetermined image processing, to generate the post-correction image AP and detect the change of the subject from the color components in the post-correction image AP.

Figure 17:
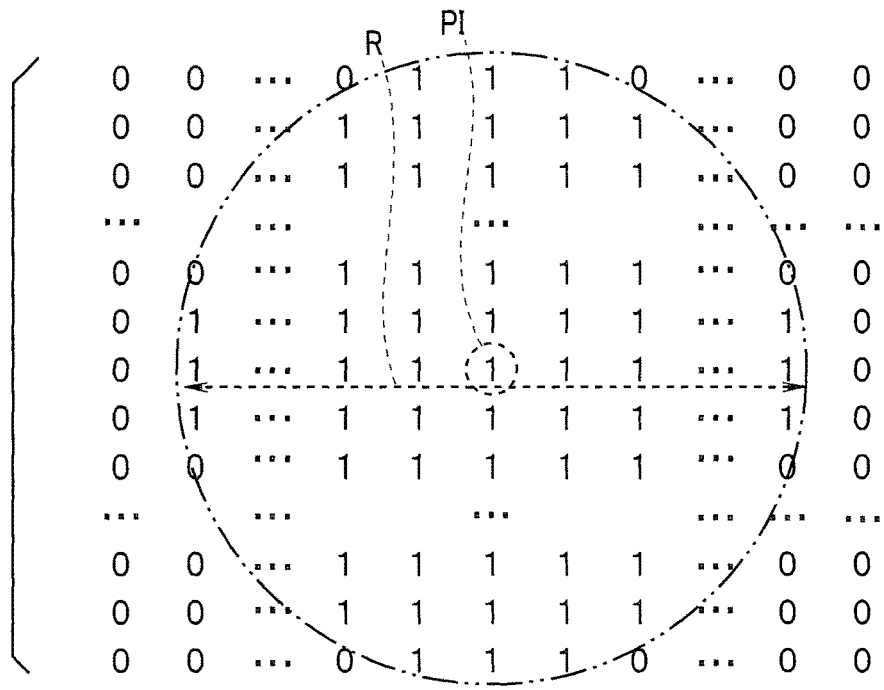
FIG. 17 is a diagram for describing a structured element according to the first embodiment of the present invention.

FIG. 17 is a diagram for illustrating a structured element. FIG. 17 illustrates a luminance information acquisition range used for image processing performed for the pre-correction image BP as a structured element parameter.

In FIG. 17, pixels within a range indicated by a dotted line respectively become structured elements when image processing is performed using contraction calculation and expansion calculation, described below, for a pixel of interest PI. In FIG. 17, a pixel indicated by numeral "1" is a pixel as a structured element.

Here, the structured element parameter is a pixel group within an area of a circle having a diameter R centered around the pixel of interest PI, and defines a range where luminance information is acquired for the pixel of interest. The diameter R is an average value of diameters of inscribed circles IC of inside closed curve edges to be analyzed, described above. Note that in FIG. 17, a pixel group within a circle indicated by a two-dot and dash line is the structured element. The pixel group indicated by numeral "1" is pixels in a range where luminance information is acquired for the pixel of interest. That is, the structured element indicates a range where the luminance information for the pixel of interest PI is acquired when predetermined calculation, described below, is performed.

The structured element designation unit 52 outputs the information about the pixel group corresponding to the diameter R as the structured element parameter to the correction image generation unit 53.

The correction image generation unit 53 performs predetermined calculation processing for an upper left pixel to a lower right pixel toward a right end from a pixel at a left end within an analysis target area AA in the pre-correction image BP and toward a line on the lowermost side from a line on the uppermost side. Here, predetermined calculation processing is opening processing. The opening processing includes processing for performing contraction processing a given number of times, e.g., three times and then performing expansion calculation the same number of times as the number of times of the contraction processing.

Figure 18:
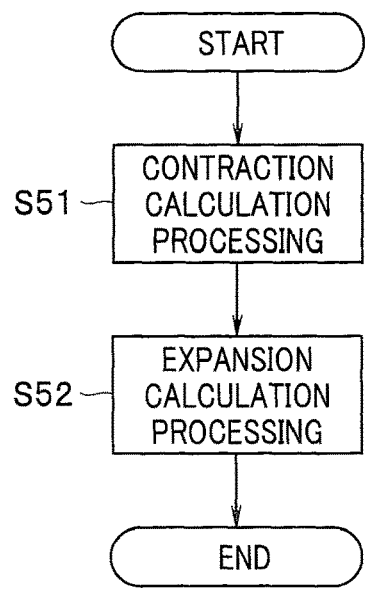
FIG. 18 is a flowchart illustrating a flow of processing for generating a correction image CP according to the first embodiment of the present invention.

FIG. 18 is a flowchart illustrating an example of a flow of processing for generating a correction image CP. The image processing unit 34 performs contraction calculation processing for a pre-correction image BP a predetermined number of times (step S51), and then performs expansion calculation processing for an image, which has been subjected to the contraction calculation processing, a predetermined number of times (step S52).

The contraction calculation processing is calculation processing for taking a minimum value of respective pixel values of a plurality of pixels within a structured element including a pixel of interest as a pixel value of the pixel of interest. The expansion calculation processing is calculation processing for taking a maximum value of the respective pixel values of the plurality of pixels within the structured element including the pixel of interest as a pixel value of the pixel of interest.

Note that when a pixel of interest PI is in a peripheral area of the pre-correction image BP, a non-existent pixel is included within an area of a circle having a diameter R. However, in such a case, processing for performing calculation using only an existent pixel, replacing the non-existent pixel with an average luminance value within the area of the circle having the diameter R, for example, is performed, so that contraction calculation and expansion processing are performed.

As described above, the correction image generation unit 53 performs contraction calculation for each of pixels and then performs similar contraction calculation two times using a structured element calculated in the structured element designation unit 52 toward the pixel at a right end from the pixel at a left end of the pre-correction image BP and toward a line on the lowermost side from a line on the uppermost side, for example. Then, the correction image generation unit 53 performs expansion calculation for each of the pixels and then performs similar expansion calculation two times using the structured element calculated in the structured element designation unit 52 in a similar order. That is, the correction image generation unit 53 performs expansion calculation once and then further two times for each of the pixels from the upper left to the lower right after performing contraction calculation three times.

A structured element used in opening processing has an average size of an inside closed curve edge in a double closed curve edge corresponding to the villus in the small intestine to be observed, which has been calculated in the structured element designation unit 52.

When the foregoing processing is performed, the correction image CP is generated.

Note that the correction image generation unit 53 may generate the correction image CP using closing processing, although the correction image generation unit 53 generates the correction image CP using the opening processing as predetermined calculation processing here.

The closing processing is processing for performing expansion calculation one or more times and then performing contraction calculation the same number of times as the number of times of the expansion calculation.

Note that in the above-described opening processing, for example, expansion calculation and contraction calculation may be performed for a plurality of pixels within a structured element including a pixel of interest, except for pixels respectively as halation elements.

Figure 19:
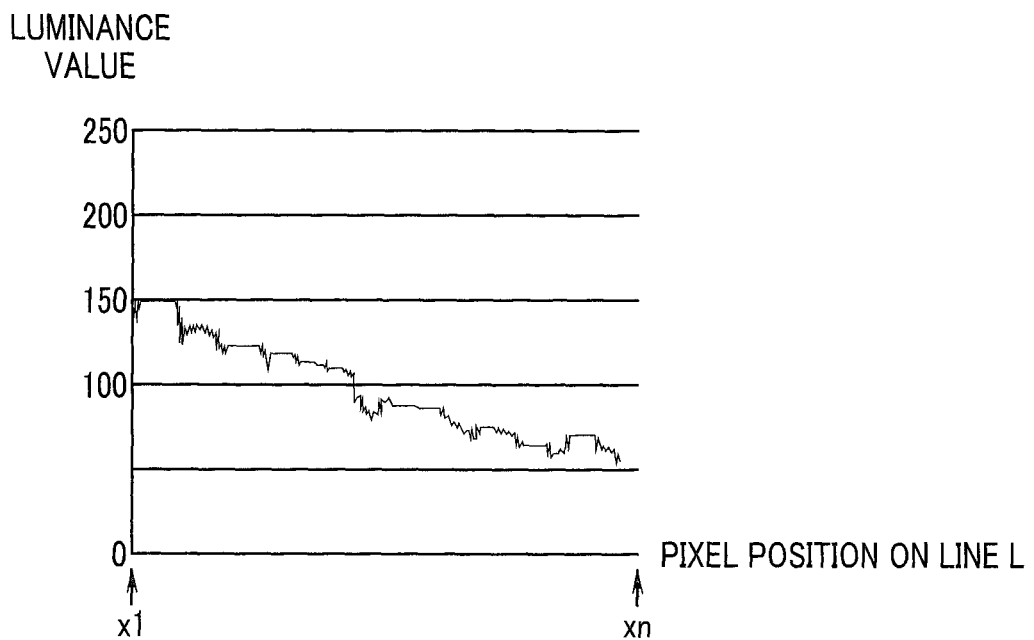
FIG. 19 is a graph illustrating a luminance distribution of a pixel group within the generated correction image CP according to the first embodiment of the present invention.

FIG. 19 is a graph illustrating a luminance distribution of a pixel group in a generated correction image CP. FIG. 19 illustrates the luminance distribution of the pixel group on the line L within the analysis target area AA in the endoscope image illustrated in FIG. 15. The correction image CP has a brightness distribution in which brightness decreases toward the right from the left. Consequently, a luminance value of the pixel group on the line L is high on the left side and is low on the right side, as illustrated in FIG. 19.

Referring to FIG. 8 again, the pre-correction image input unit 61 in the image processing unit 34 receives as input the pre-correction image BP, the correction image input unit 62 receives as input the correction image CP generated in the signal generation unit 33 (the correction data generation section), and the image difference extraction unit 63 extracts a difference image between the pre-correction image BP and the correction image CP in the analysis target area AA (step S17).

In step S16, the correction image CP1 for the first image IMG1 and the correction image CP2 for the second image IMG2 are generated. In step S17, a difference between each of pixels in the pre-correction image BP1 and a corresponding pixel in the correction image CP1 and a difference between each of pixels in the pre-correction image BP2 and a corresponding pixel in the correction image CP2 are taken for each of the first image IMG1 and the second image IMG2, to respectively extract difference images and generate the post-correction images AP1 and AP2.

Figure 20:
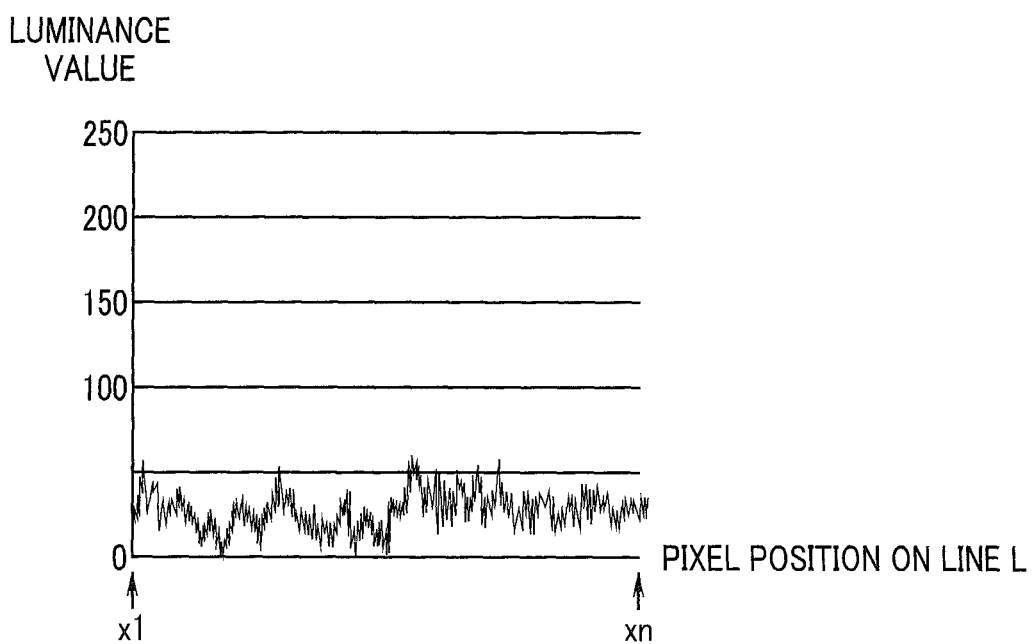
FIG. 20 is a graph illustrating a luminance distribution of a pixel group within a generated post-correction image AP according to the first embodiment of the present invention.

FIG. 20 is a graph illustrating a luminance distribution of a pixel group in a generated post-correction image AP. FIG. 20 illustrates the luminance distribution of the pixel group on the line L within the analysis target area AA in the endoscope image illustrated in FIG. 15. The post-correction image AP is an image in which luminance unevenness by a light distribution characteristic of illumination light, for example, has been more suppressed than the endoscope image illustrated in FIG. 16.

The color component value extraction unit 71 in the distribution characteristic value calculation unit 35 extracts color component values, e.g., an R component value, a G component value, and a B component value of each of pixels in each of the post-correction image AP1 and the post-correction image AP2 (step S18).

That is, the color component value extraction unit 71 extracts respective color component values (an R component value, a G component value, and a B component value) of each of pixels composing the post-correction image AP1 and respective color component values (an R component value, a G component value, and a B component value) of each of pixels composing the post-correction image AP2.

Then, the total luminance value calculation unit 72 in the distribution characteristic value calculation unit 35 calculates a total luminance value (first total luminance value) of the respective color component values relating to the post-correction image AP1 and a total luminance value (second total luminance value) of the respective color component values relating to the post-correction image AP2, which have been extracted in the color component value extraction unit 71.

The luminance value distribution characteristic value calculation unit 73 in the distribution characteristic value calculation unit 35 extracts the total luminance values calculated in the total luminance value calculation unit 72, i.e., respective distribution characteristic values, i.e., a first distribution characteristic value and a second distribution characteristic value relating to the first total luminance value and the second total luminance value (step S19).

Note that in the present embodiment, as described above, a "distribution characteristic value" is found as a standard deviation or a dispersion of a pixel value distribution of a plurality of pixels within the analysis target area AA. That is, the distribution characteristic value calculation unit 35 extracts color components in the analysis target area AA in the post-correction image AP1 as the first processed image to find the first distribution characteristic value while extracting color components in the analysis target area AA in the post-correction image AP2 as the second processed image to find the second distribution characteristic value.

Figure 21:
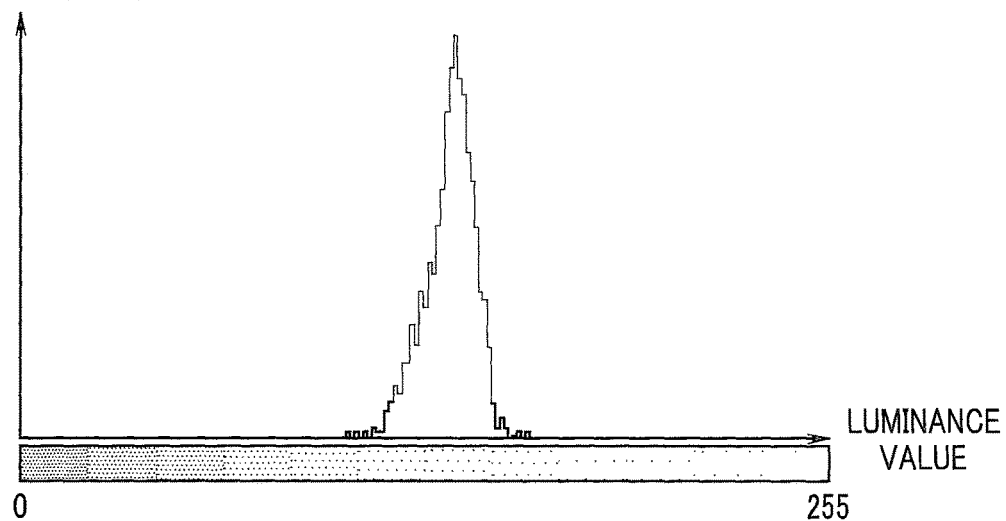
FIG. 21 is a histogram of a luminance value in a post-correction image AP1 before a predetermined load (predetermined function) is applied to a subject according to the first embodiment of the present invention.
Figure 22:
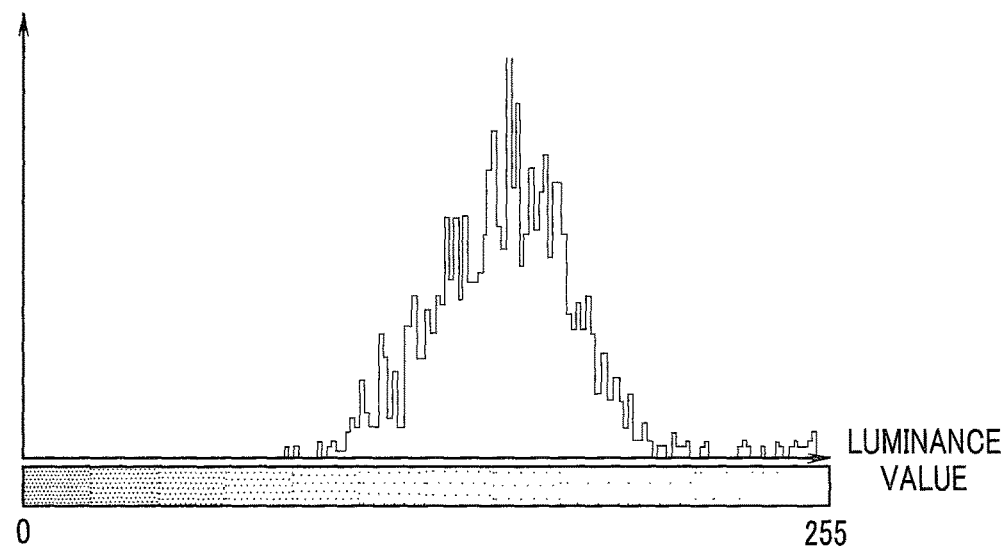
FIG. 22 is a histogram of a luminance value in a post-correction image AP2 after a predetermined load (predetermined function) is applied to a subject according to the first embodiment of the present invention.

FIG. 21 is a histogram of a luminance value in the post-correction image AP1 before a predetermined load (predetermined function) is applied to a subject. FIG. 22 is a histogram of a luminance value in the post-correction image AP2 after the predetermined load (predetermined function) is applied to the subject.

FIGS. 21 and 22 are each a histogram in which a vertical axis represents a luminance value in a target area of each of the post-correction image AP1 and the post-correction image AP2 and a horizontal axis represents a number of pixels corresponding to the luminance value. FIG. 22 in which the load has been applied indicates that a standard deviation of the luminance value is larger, i.e., an amount of change of a distribution characteristic value is larger than the standard deviation, i.e., the amount of change of a distribution characteristic value in FIG. 21 in which the load has not been applied.

Then, the image analysis unit 36 calculates an amount of change in a distribution characteristic value calculated in the luminance value distribution characteristic value calculation unit 73 in the following manner, for example, as a degree of change of a post-load image from a pre-load image (step S20).

That is, when the first distribution characteristic value relating to the post-correction image AP1 for the first image IMG1 (pre-load image) and the second distribution characteristic value relating to the post-correction image AP2 for the second image IMG2 (post-load image), which have been calculated in the luminance value distribution characteristic value calculation unit 73, are respectively taken as <1> and <2>, the image analysis unit 36 calculates the amount of change, as expressed by the following equation 1, as an absolute value of a difference between the first distribution characteristic value and the second distribution characteristic value.

$$\text{Amount of change} = <2> - <1> \qquad \text{[Equation 1]}$$

The amount of change in the distribution characteristic value between the pre-load image and the post-load image, which has been obtained in step S20, does not include a brightness distribution of an image by a light distribution characteristic of illumination, for example.

The image analysis unit 36 determines whether a disqualified element such as halation exists within the post-correction image AP1 for the first image IMG1 and the post-correction image AP2 for the second image IMG2 (step S21). When a pixel value is a value within a range from 0 to 255, it is determined that in the post-correction image AP as a difference image, a pixel having a pixel value of 100 or more is a disqualified pixel using 100, for example, as a threshold value.

The image analysis unit 36 excludes, if at least one of the respective post-correction images AP1 and AP2 for the first image IMG1 and the second image IMG2 includes a disqualified element such as halation, i.e., a disqualified pixel, the disqualified pixel from the post-correction image AP1 and the post-correction image AP2 (step S22), and performs respective processes in steps S19 and S20 for a pixel group excluding the disqualified pixel. That is, the distribution characteristic value calculation unit 35 excludes the disqualified element unsuited to extract respective color component values in the post-correction image AP1 and the post-correction image AP2, to extract the first and second distribution characteristic values.

Note that after step S22, color components in the analysis target area may be extracted again in step S18, and the processes in steps S19 and S20 may be performed based on the extracted color component.

Note that if it is determined that a disqualified element is included in the process in step S20, a message or the like notifying that at least one of the post-correction image AP1 and the post-correction image AP2 includes a disqualified element may be displayed on the display apparatus 5, to make the user select whether a process in step S22 is to be performed.

After the processes in steps S19 and S20 are performed for a pixel group including no disqualified element such as halation, display image generation processing for generating an image to be displayed on the display apparatus 5 is performed (step S23). The display image generation processing is processing for generating an image, as illustrated in FIG. 23, to generate an image to be displayed based on image data corresponding to a frame used in processes in steps S11 to S22 in a period of t seconds, e.g., a period of one second as a predetermined execution period and update the image to be displayed on the display apparatus 5.

After step S23, it is determined whether information about the image or the like continues to be displayed based on determination by the video processor 3 or judgment by the user (step S24). If the display is continued, the processing returns to step S11. In step S11 and the subsequent steps, the above-described processing is performed again.

Figure 23:
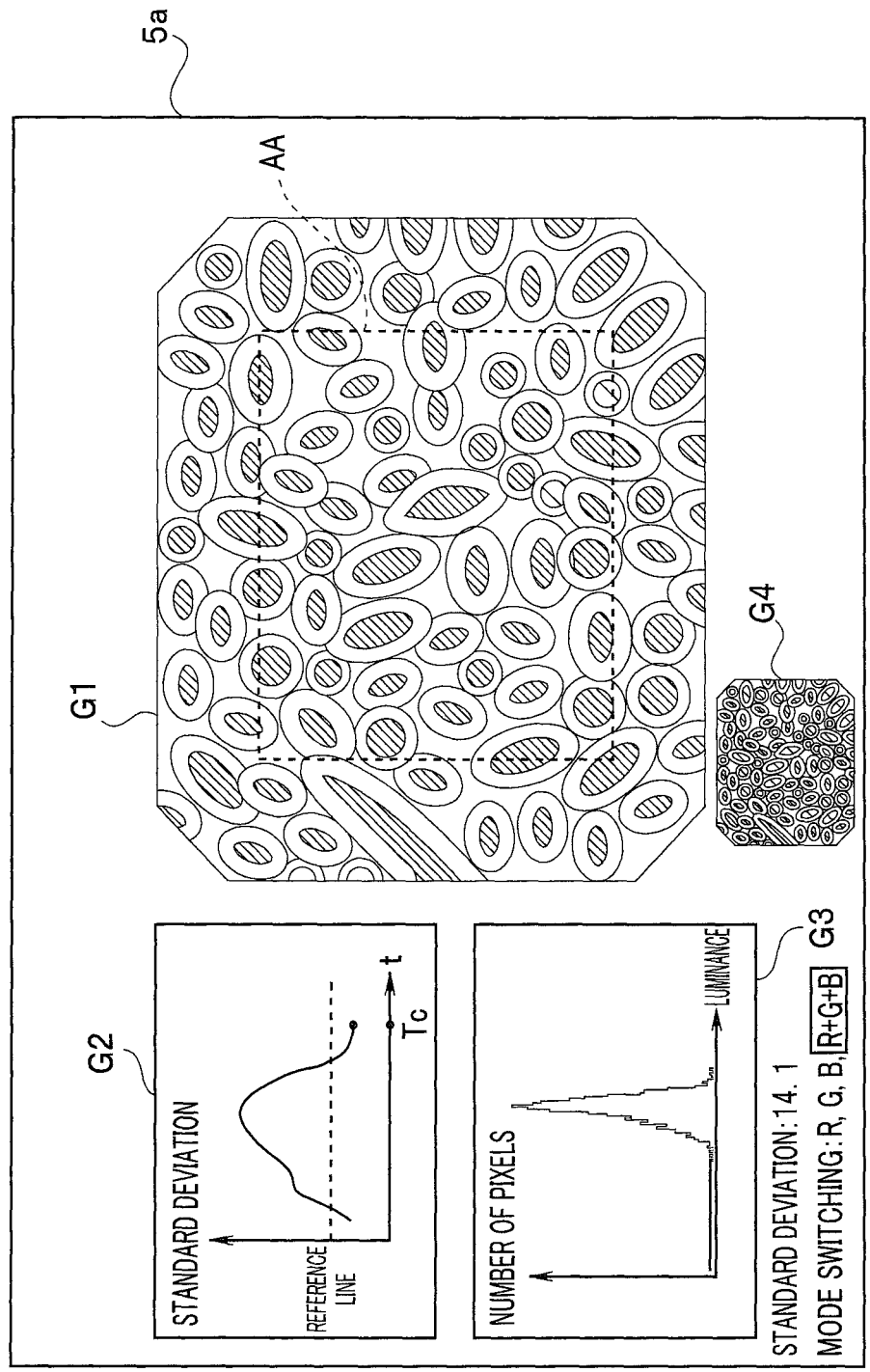
FIG. 23 is a diagram illustrating an example of a user interface representing a change in color components of a subject during enlarged observation displayed on a display apparatus 5 according to the first embodiment of the present invention.

FIG. 23 is a diagram illustrating an example of a user interface representing a change in color components of a subject during enlarged observation displayed on the display apparatus 5.

When the user selects a predetermined display mode during endoscope inspection, a color change display mode screen as illustrated in FIG. 23 is displayed on the display screen 5a of the display apparatus 5. On the color change display mode screen displayed on the display screen 5a, a live image display portion G1, a standard deviation graph display portion G2, a luminance distribution display portion G3 representing a distribution of luminance values in a live image, and a display portion G4 where a pre-correction image BP1 or a post-correction image AP1 for the first image IMG1 is displayed are displayed.

The live image display portion G1 is an area on which a live image of an endoscope image obtained from the endoscope 2 is displayed. That is, the endoscope image in real time is displayed on the live image display portion G1.

The standard deviation graph display portion G2 is an area representing a change in a standard deviation of respective pixel values of a plurality of pixels within an analysis target area AA along a lapse of time t of the endoscope image. The standard deviation in the standard deviation graph display portion G2 is a standard deviation of a luminance value relating to a total value of respective color component values of a plurality of pixels within the analysis target area AA sampled at a plurality of timings including the processing timing in step S19 illustrated in FIG. 8, described above, e.g., at a timing for approximately second. Here, a standard deviation in a predetermined period in the past from a current time point Tc is displayed. The standard deviation as the distribution characteristic value calculated in the image analysis unit 36 becomes larger and then becomes smaller than a reference line after spraying of glucose when a standard deviation before spraying of glucose is indicated as a reference line. Thus, the standard deviation graph display portion G2 indicates how the standard deviation changes up to the current time point Tc.

On the luminance distribution display portion G3, a distribution and a standard deviation of the luminance values of the live image displayed on the live image display portion G1 are displayed in real time. The luminance value distribution on the luminance distribution display portion G3 is also determined based on the luminance value related to the total value of the respective color component values in the post-correction image AP sampled at a plurality of timings including the processing timing in step S19 illustrated in FIG. 8, described above. A difference in color shading within an analysis target area is small in an image before spraying of glucose, as illustrated in FIG. 21, and an increase in an amount of blood within the villus occurs by spraying of a medicinal solution in an image after the spraying. Thus, a difference in color shading increases within the villus included in the analysis target area. In the display of the standard deviation, an optimum mode may be selected to match an observation target because modes can be switched for each of the color components. The luminance distribution display portion G3 displays such a state of the distribution of the luminance values in real time.

Note that the pre-correction image BP1 or the post-correction image AP1 for the first image IMG1 sampled at a plurality of timings including the processing timing in step S19 illustrated in FIG. 8, described above, e.g., at a timing for approximately one second, on the live image display portion G1 may also be displayed on the display portion G4.

Furthermore, on the standard deviation graph display portion G2 and the luminance distribution display portion G3, the standard deviation and the luminance values of the plurality of pixels within the analysis target area AA may also be displayed by being respectively calculated and extracted based on the endoscope image obtained in real time.

The color change display mode screen enables the user to detect the change in the color components of the subject while confirming transition of the standard deviation and a state of the luminance distribution.

As described above, according to the above-described embodiment, the change in the color components of the subject can be detected using an image a brightness distribution of which is not affected by the light distribution characteristic of illumination or a distance from the distal end portion of the insertion section to the observation target, for example.

Particularly when the subject is not fixed or when the distance between the subject and the distal end portion of the insertion section easily changes, like at the time of the enlarged observation mode, the change in the color components of the subject can also be detected using the image the brightness distribution of which is not affected by the light distribution characteristic of illumination, for example.

The correction image CP is generated using the structured element which matches the analysis target. Thus, the post-correction image AP from which an influence on the brightness distribution of the image by the light distribution characteristic of illumination light, for example, has been removed is obtained while leaving a characteristic of a luminance within the subject (e.g., the villus in the small intestine), and as a result, the color components of the subject image acquired time-sequentially may be extracted accurately.

Note that although the structured element is determined in real time based on the image in the above-described example, the user may view the image and the structured element corresponding to the distance from the distal end portion of the insertion section to an object may be used by inputting or selecting the distance.

A modification to the above-described embodiment will be described below.

(Modification 1a)

In the above-described embodiment, the pre-correction image acquisition unit 51 acquires the image obtained by the endoscope 2 as the pre-correction image BP, and the pre-correction image BP is supplied as it is to the structured element designation unit 52 and the correction image generation unit 53. On the other hand, a signal generation unit 33 in a modification 1a is configured to correct luminance unevenness by a light distribution characteristic obtained by simulation or by actual equipment for a pre-correction image BP of an image obtained by the endoscope 2 and supply a corrected pre-correction image BPP to a structured element designation unit 52 and a correction image generation unit 53.

Figure 24:
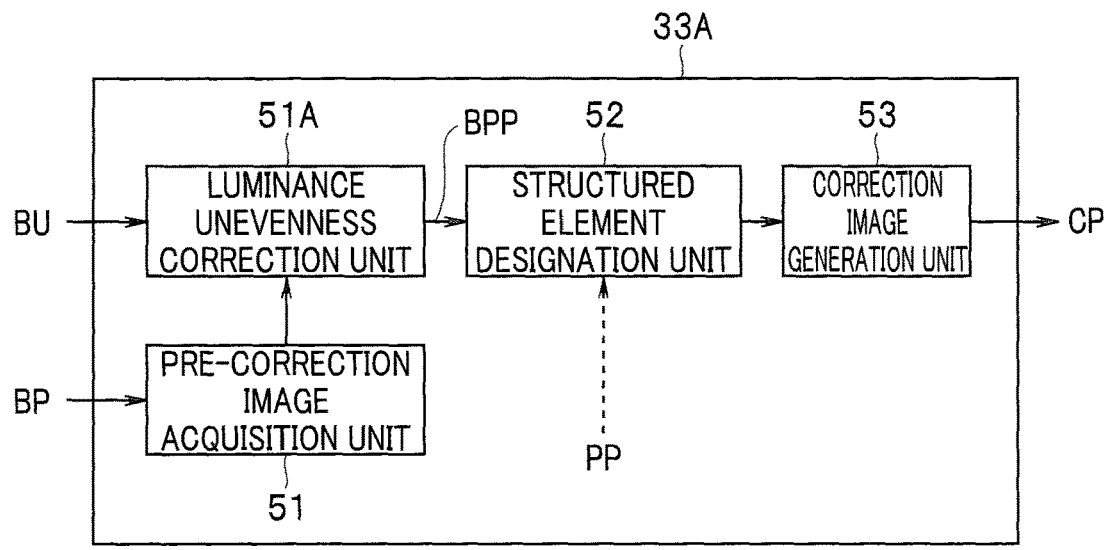
FIG. 24 is a block diagram of a signal generation unit 33A according to a modification 1a to the first embodiment of the present invention.

Only a configuration according to the modification 1a will be described below. FIG. 24 is a block diagram of a signal generation unit 33A according to the modification 1a. A pre-correction image BP acquired in a pre-correction image acquisition unit 51 is inputted to a luminance unevenness correction unit 51A configured to correct luminance unevenness due to a light distribution characteristic. Luminance unevenness data BU and the pre-correction image BP from the pre-correction image acquisition unit 51 are inputted to the luminance unevenness correction unit 51A, and the pre-correction image BP is corrected to suppress luminance unevenness due to a light distribution characteristic of illumination light based on the luminance unevenness data BU so that a pre-correction image BPP having no luminance unevenness is generated.

The luminance unevenness correction unit 51A is a processing unit configured to perform correction to eliminate the luminance unevenness due to the light distribution characteristic of illumination light obtained by simulation or actual measurement for a first image IMG1 and a second image IMG2 inputted to an image input unit 32.

Figure 25:
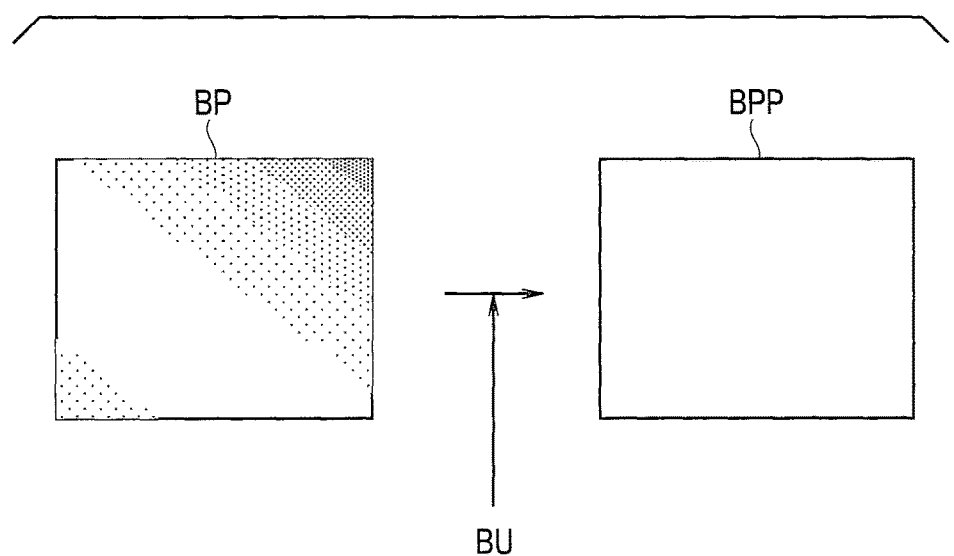
FIG. 25 is a diagram for describing processing for generating a pre-correction image BPP having no luminance unevenness according to the modification 1a to the first embodiment of the present invention.

FIG. 25 is a diagram for describing processing for generating the pre-correction image BPP having no luminance unevenness. As illustrated in FIG. 25, the pre-correction image BP originally has luminance unevenness due to a light distribution characteristic. In FIG. 25, the pre-correction image BP has such luminance unevenness that the upper right becomes dark. The luminance unevenness correction unit 51A corrects the pre-correction image BP such that luminance unevenness is eliminated using the luminance unevenness data BU, to generate the pre-correction image BPP having no luminance unevenness. That is, the signal generation unit 33A functions as a correction data generation section, to generate correction images CP1 and CP2 respectively as first and second brightness distribution correction data using the first image IMG1 and the second image IMG2 luminance unevenness of which has been corrected by the luminance unevenness correction unit 51A.

The luminance unevenness data BU may be data obtained by light distribution simulation of light which passes through an illumination optical system in a distal end portion of an insertion section of the endoscope 2 or may be data obtained by actually measuring a light distribution of illumination light of the endoscope 2.

The luminance unevenness changes depending on a distance between an object and the distal end portion of the insertion section. Thus, the luminance unevenness data BU for each distance is set by simulation calculation or actual measurement.

The luminance unevenness data BU can be generated by simulation for each distance in the simulation calculation.

The luminance unevenness data BU can be generated from an endoscope image obtained by arranging a white balance cap, for example, in the distal end portion of the insertion section of the endoscope 2 or in the vicinity of the distal end portion when actually measured and performing image pickup for each distance.

Viewing the endoscope image, a user selects or designates the luminance unevenness data BU to be used depending on the size of an object (e.g., villus in small intestine), i.e., depending on a distance from the distal end portion of the insertion section to the object which has been estimated by seeing an image of the object.

As a result, the luminance unevenness correction unit 51A removes a brightness distribution which the pre-correction image BP originally has by the selected luminance unevenness data BU, to output pre-correction image BPP having no luminance unevenness.

According to the modification 1a, the pre-correction image BPP having no luminance unevenness is supplied to a structured element designation unit and correction image generation unit 53. Thus, a change of color components of a subject can be more accurately detected.

(Modification 1b)

In the above-described embodiment, one or a plurality of analysis target areas AA are set within an image obtained by the endoscope 2. On the other hand, in a modification 1b, respective areas in a plurality of inside closed curve edges within a plurality of double closed curve edges extracted from an image obtained by the endoscope 2 are each set as an analysis target area AAs.

That is, the area, i.e., a central portion in the inside closed curve edge within each of the double closed curve edges can be extracted by a double closed curve edge specifying unit 85, described above. Accordingly, the areas within the plurality of inside closed curve edges specified by the double closed curve edge specifying unit 85 are each extracted as an analysis target area AAs as an area where color components are accurately extracted.

In step S15 in which an analysis target area is set, a plurality of areas surrounded by closed curves in each of first and second processed images are extracted, and a predetermined number of central portions, which are each surrounded by an annular peripheral portion and different in color from the peripheral portion, are extracted from each of the areas, to determine the plurality of central portions as the analysis target area AAs.

A signal generation unit 33 functions as a correction data generation section, to perform the above-described processing for areas in a plurality of inside closed curve edges in a pre-correction image BP to generate a correction image CP. The image processing unit 34 generates a post-correction image AP from a difference between the pre-correction image BP and the correction image CP.

A distribution characteristic value of the post-correction image AP may be a distribution characteristic value of the entire areas in the plurality of inside closed curve edges included in the analysis target area AA or may be an average value of respective distribution characteristic values in the inside closed curve edges.

According to the modification 1b, a change in color components of a subject can be detected using an image a brightness distribution of which is not affected by a light distribution characteristic of illumination, for example.

Second Embodiment

Although the correction image CP is generated by performing image processing such as opening processing using the structured element from the pre-correction image BP in the first embodiment, a correction image CP is generated based on a plurality of pixel values at a sampling point on a pre-correction image BP in the present embodiment.

An endoscope system according to the present embodiment has substantially the same configuration as the configuration of the endoscope system according to the first embodiment, and hence the same components are assigned the same reference numerals to describe only different components.

The endoscope system according to the present embodiment differs in only a configuration of the signal generation unit from the endoscope system 1 according to the first embodiment.

Figure 26:
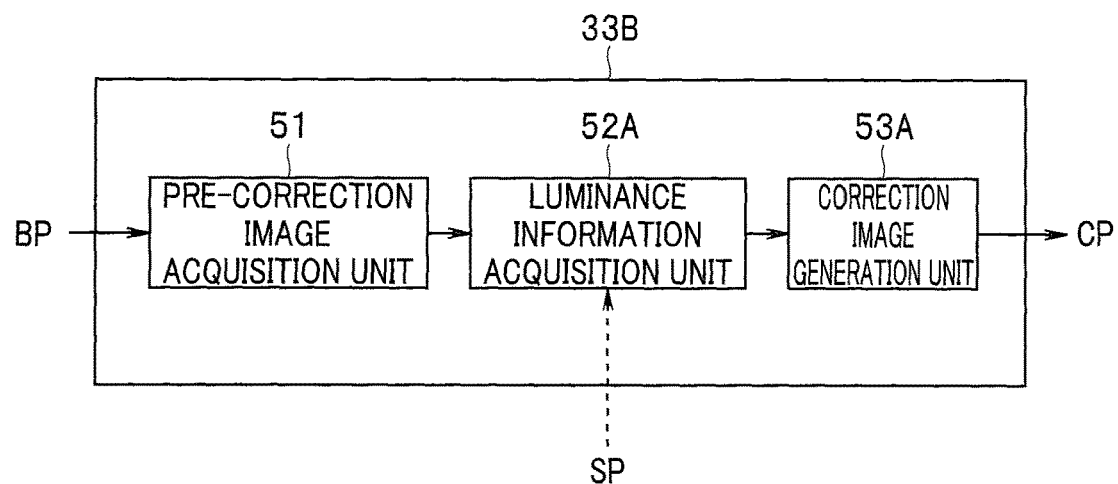
FIG. 26 is a block diagram of a signal generation unit 33B according to a second embodiment of the present invention.

FIG. 26 is a block diagram of a signal generation unit 33B. The signal generation unit 33B includes a pre-correction image acquisition unit 51, a luminance information acquisition unit 52A, and a correction image generation unit 53A (a correction image generation unit). A pre-correction image BP acquired in the pre-correction image acquisition unit 51 is inputted to the luminance information acquisition unit 52A, and the luminance information acquisition unit 52A acquires luminance information about a plurality of points SP designated.

Figure 27:
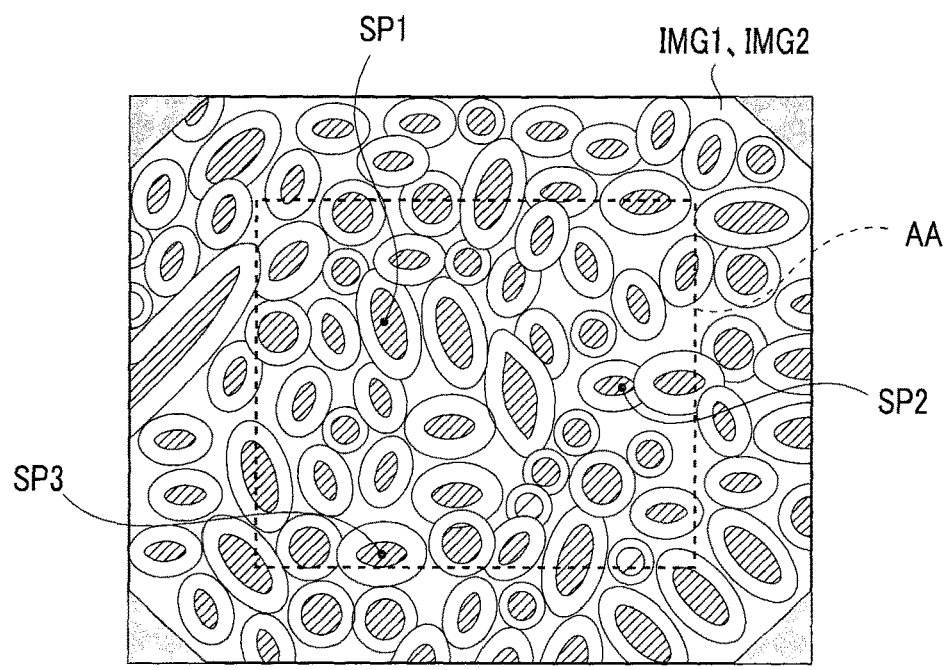
FIG. 27 is a diagram for describing three points designated in a pre-correction image BP according to the second embodiment of the present invention.

FIG. 27 is a diagram for describing three points designated in a pre-correction image BP. FIG. 27 illustrates a case where three points SP1, SP2, and SP3 are designated as a plurality of points SP at which luminance information is acquired. The plurality of points SP may be designated on a screen by a user, or may be respectively points previously set within an analysis target area AA.

The correction image generation unit 53A in the signal generation unit 33B calculates a plane determined by respective luminance values at the designated three points SP1, SP2, and SP3, and generates a correction plane, i.e., a correction image CP corresponding to a direction of slope and a size of the calculated plane. That is, the correction image CP generated by the correction image generation unit 53A is an image which defines a luminance distribution by the slope of the plane determined by the luminance values at the three points SP1, SP2, and SP3.

The signal generation unit 33B generates first and second brightness distribution correction data (CP1 and CP2) based on a difference among respective brightnesses at a plurality of points in each of a first image IMG1 and a second image IMG2.

The correction image generation unit 53A generates a correction image CP1 as the first brightness distribution correction data for correcting a brightness distribution where brightness has an overall slope of the first image IMG1 to suppress an optical influence on color components composing the first image IMG1 using the respective luminance values at the three points SP1, SP2, and SP3 of the first image IMG1 while generating a correction image CP2 as the second brightness distribution correction data for correcting a brightness distribution where brightness has an overall slope of the second image IMG2 to suppress an optical influence on color components composing the second image IMG2 using respective luminance values at three points SP1', SP2', and SP3' of the second image IMG2.

The image processing unit 34 generates post-correction images AP1 and AP2 from respective pre-correction images BP1 and BP2 for the first image IMG1 and the second image IMG2 using the correction image CP generated by the correction image generation unit 53A.

Accordingly, according to the second embodiment, a change of color components of a subject can also be detected using an image a brightness distribution of which is not affected by a light distribution characteristic of illumination, for example.

Then, a modification applicable to the first and second embodiments will be described.

(Modification 1)

Although the color components in the image of the subject are detected in the observation mode using light in two narrow bands, specifically light in a narrow band other than respective wavelength bands of 415 nm and 540 nm in the first and second embodiments and the respective modifications, described above, the above-described first and second embodiments and respective modifications are also applicable to detection of color components in an image of a subject obtained in an observation mode using light in a narrow band other than the two wavelength bands.

Furthermore, the above-described respective embodiments and respective modifications are also applicable to a case where a change of a subject is detected from an endoscope image obtained in not an NBI mode but a normal light observation mode with white light.

Furthermore, the above-described respective embodiments and respective modifications are also applicable to detection of a change of color components in an image of a subject obtained in another special light observation such as fluorescence observation and infrared light observation.

(Modification 2)

Although the change of the color components in the image of the subject is detected at the time of the enlarged observation mode of the subject in the above-described first and second embodiments and respective modifications, the above-described respective embodiments and respective modifications are also applicable in a mode other than the enlarged observation mode of the subject, i.e., a normal observation mode.

(Modification 3)

Although the total value of the R, G, and B color components is used as color components in an image in the above-described first and second embodiments and respective modifications, respective RGB color components may be used to calculate respective distribution characteristic values for the RGB color components and detect a change in each of the distribution characteristic values.

(Modification 4)

Although the degree of the change has been detected for the image of the subject by applying a predetermined load to a desired observation site when endoscope observation is being performed and suppressing an influence on a deviation of brightness of an image by a light distribution characteristic of illumination, for example, for a first image IMG1 and a second image IMG2 obtained before and after the load (function) is applied in the above-described first and second embodiments and respective modifications, an image when the endoscope observation has been performed may be recorded on a storage device, to detect the color components of the image of the subject, described above, for the first image IMG1 and the second image IMG2 selected from the recorded image after inspection. In other words, the color components of the image of the subject may be detected in real time so-called online during the inspection of the subject or may be detected offline after the inspection.

Accordingly, the change of the color components of the subject can be detected using the image the brightness distribution of which is not affected by the light distribution characteristic of illumination, for example, even in the above-described respective embodiments and respective modifications.

That is, a user may continuously acquire an image, which is being inspected, while applying a predetermined load to a desired observation site and record the image in a storage device such as a hard disk device during observation of an inside of a subject, to end the inspection once, and perform the above-described image processing for the image recorded on the storage device so-called offline after the inspection.

As described above, according to the above-described respective embodiments and respective modifications, an image analysis apparatus capable of suppressing an influence on a deviation of brightness of an endoscope image by a light distribution characteristic of illumination light, for example, and accurately extracting a degree of change for an image of a subject time-sequentially acquired, and an image analysis system, and a method for operating the image analysis apparatus can be provided.

Note that the whole or a part of a program for performing the above-described operation is recorded or stored in a portable medium such as a flexible disk or a CD-ROM, or a storage medium such as a hard disk as a computer program product. The program is read by a computer so that the whole or a part of an operation is performed. Alternatively, the whole or the part of the program can be distributed or provided via a communication network. A user can easily implement an image processing apparatus according to the present invention, for example, by downloading the program via the communication network to install the program into the computer or installing the program into the computer from the recording medium.

The present invention is not limited to the above-described embodiments, but various changes, alterations, and the like are enabled without departing from the scope and spirit of the present invention.

What is claimed is:

1. An image analysis apparatus comprising:
a processor including hardware, wherein
the processor
receives a first image of a subject acquired by an endoscope at a first timing and a second image of the subject acquired by the endoscope at a second timing later than the first timing,
generates first brightness distribution correction data for correcting a slope of a brightness distribution of the received first image using the first image and generates second brightness distribution correction data for correcting a slope of a brightness distribution of the second image using the second image,
generates a first processed image obtained by causing the first brightness distribution correction data to act on the first image and a second processed image obtained by causing the second brightness distribution correction data to act on the second image,
analyzes a degree of change between the first processed image and the second processed image, and
extracts areas respectively surrounded by closed curves extracted from the first image and the second image to generate the first brightness distribution correction data and the second brightness distribution correction data based on a size of each of the extracted areas.

2. The image analysis apparatus according to claim 1, wherein the processor extracts the areas respectively surrounded by the closed curves extracted from the first image and the second image and generates the first brightness distribution correction data and the second brightness distribution correction data based on respective average sizes of inscribed circles of the extracted areas.

3. The image analysis apparatus according to claim 1, wherein the processor extracts color components in the first processed image to find a first distribution characteristic value and extracts color components in the second processed image to find a second distribution characteristic value.

4. The image analysis apparatus according to claim 3, wherein
the processor sets at least one analysis target area in each of the first image and the second image, and
the processor extracts color components in the at least one analysis target area in the first processed image to find the first distribution characteristic value and extracts color components in the at least one analysis target area in the second processed image to find the second distribution characteristic value.

5. The image analysis apparatus according to claim 4, wherein the processor sets the analysis target area in plurality for each of the first image and the second image, and the processor generates the first brightness distribution correction data and the second brightness distribution correction data for each analysis target area set in each of the first image and the second image.

6. The image analysis apparatus according to claim 1, wherein
the processor performs correction for eliminating luminance unevenness due to a light distribution characteristic of illumination light obtained by simulation or actual measurement for the first image and the second image, and
the processor generates the first brightness distribution correction data and the second brightness distribution correction data respectively using the first image and the second image the luminance unevenness of which is corrected.

7. The image analysis apparatus according to claim 1, wherein the processor generates the first brightness distribution correction data and the second brightness distribution correction data based on a difference among brightnesses at a plurality of points in each of the first image and the second image.

8. The image analysis apparatus according to claim 3, wherein the first distribution characteristic value and the second distribution characteristic value are respectively standard deviations or dispersions of luminance distributions of the color components in the first processed image and the second processed image.

9. The image analysis apparatus according to claim 4, wherein the processor extracts a plurality of areas respectively surrounded by closed curves in each of the first processed image and the second processed image and extracts from each of the areas a predetermined number of central portions each surrounded by an annular peripheral portion and different in color from the peripheral portion, to respectively determine each of the plurality of central portions as the analysis target area.

10. The image analysis apparatus according to claim 3, wherein the processor extracts the first distribution characteristic value and the second distribution characteristic value, except for a disqualified element unsuited to extract respective color component values in the first processed image and the second processed image.

11. The image analysis apparatus according to claim 1, wherein the processor receives, from among images of the subject acquired by the endoscope, the first image and the second image as input, excluding an image including a predetermined number or more of disqualified elements each unsuited to extract color component values.

12. The image analysis apparatus according to claim 1, wherein a subject image acquisition unit configured to acquire an image of the subject and an illumination window configured to illuminate the subject are arranged on a same surface at a distal end of the endoscope.

13. The image analysis apparatus according to claim 1, wherein the first image and the second image are each an image of reflected light when the subject is illuminated with illumination light in a narrower predetermined wavelength band than white light.

14. The image analysis apparatus according to claim 1, wherein the subject into which the endoscope is inserted is an intestinal tract of a living body, and the first image and the second image are each an image including an image of villus existing on an inner surface of the intestinal tract.

15. An image analysis system comprising:
the image analysis apparatus according to claim 1; and
the endoscope, which is inserted into a subject and picks up and acquires an image within the subject.

16. A method for operating an image analysis apparatus, the method comprising:
receiving a first image of a subject acquired by an endoscope at a first timing and a second image of the subject acquired by the endoscope at a second timing later than the first timing;
generating first brightness distribution correction data for correcting a slope of a brightness distribution of the received first image using the first image and generating second brightness distribution correction data for correcting a slope of a brightness distribution of the second image using the second image;
generating a first processed image obtained by causing the first brightness distribution correction data to act on the first image and a second processed image obtained by causing the second brightness distribution correction data to act on the second image; and
analyzing a degree of change between the first processed image and the second processed image,
wherein in the generating of the first brightness distribution correction data and in the generating of the second brightness distribution correction data, areas respectively surrounded by closed curves extracted from the first image and the second image are extracted, and the first brightness distribution correction data and the second brightness distribution correction data are generated based on a size of each of the extracted areas.

* * * * *